(12) United States Patent
Schoenhofen et al.

(10) Patent No.: US 8,952,183 B2
(45) Date of Patent: Feb. 10, 2015

(54) INHIBITORS OF SIALIDASE OR SIALIDASE-LIKE ENZYMES

(75) Inventors: Ian C. Schoenhofen, Ottawa (CA); Dennis M. Whitfield, Ottawa (CA); Susan M. Logan, Ottawa (CA)

(73) Assignee: National Research Council of Canada, Ottawa, Ontario ( * ) Notice: Subject to any disclaimer, the term of this patent is extended or adjusted under 35 U.S.C. 154(b) by 139 days.

(21) Appl. No.: 13/266,383

(22) PCT Filed: May 4, 2010

(86) PCT No.: PCT/CA2010/000680
§ 371 (c)(1), (2), (4) Date: Oct. 26, 2011

(87) PCT Pub. No.: WO2010/127443
PCT Pub. Date: Nov. 11, 2010

(65) Prior Publication Data
US 2012/0046355 A1    Feb. 23, 2012

Related U.S. Application Data

(60) Provisional application No. 61/213,070, filed on May 4, 2009.

(51) Int. Cl.
*C07D 315/00* (2006.01)
*A61K 31/35* (2006.01)
*C07D 309/30* (2006.01)

(52) U.S. Cl.
CPC ................................. *C07D 309/30* (2013.01)
USPC ........................... 549/419; 549/420; 514/459

(58) Field of Classification Search
USPC ..................... 549/419, 420; 514/459
See application file for complete search history.

(56) References Cited

U.S. PATENT DOCUMENTS 5,648,379 A * 7/1997 Von Itzstein et al. ......... 514/459
5,990,156 A * 11/1999 Cherry et al. ................. 514/459
7,045,535 B2 * 5/2006 Chand et al. .................. 514/326

FOREIGN PATENT DOCUMENTS

| CA | 2760106 | 5/2010 |
| WO | 2010/069047 | 6/2010 |
| WO | 2010/127443 | 11/2010 |

OTHER PUBLICATIONS

European Patent Office Communication dated Dec. 15, 2011 for 10771936.1.
International Search Report dated Jul. 8, 2010 for PCT/CA2010/000680.
Written Opinion dated Jul. 28, 2010 for PCT/CA2010/000680.
International Preliminary Examination Report dated Nov. 9, 2011 for PCT/CA2010/000680.
Aktas, M., and Narberhaus, F., Expression and Physiological Relevance of *Agrobacterium tumefaciens* Phosphatidylcholine Biosynthesis Genes, J. Bacteriol., 191, 2033 (2009).
Beau, J-M., et al., Chemical behaviour of cytidine ~'-monophospho-~-acety~-~-~-neuarcaidm ~n~c under neutral and alkaline conditions, Eur. J. Biochem. 140, 203 (1984).
Beynon, L.M., et al., The structure of the lipopolysaccharide 0 antigen from *Yersinia ruckeri* serotype 01, Carbohydr. Res. 256, 303 (1994).
Buxton, R.C., et al., Development of a Sensitive Chemiluminescent Neuraminidase Assay for the Determination of Influenza Virus Susceptibility to Zanamivir, Anal. Biochem. 280, 291 (2000).
Colman, P.M., Influenza virus neuraminidase: Structure, antibodies, and inhibitors, Protein Science 3, 1687 (1994).
Colman, P.M., A novel approach to antiviral therapy for influenza, J. Antimicrob. Chemother. 44, 17 (1999).
Gubareva, L.V., et al, Influenza virus neuraminidase inhibitors, Lancet 355, 827 (2000).
Hashem, A.M., et al., Aurintricarboxylic Acid is a Potent Inhibitor of Influenza A and B Virus Neuraminidases, PLoS ONE 4, e8350 (2009).
Hashii, N., et al., Structure and serological characterization of 5,7-diamino-3,5,7,9-tetradeoxy-non-2-ulosonic acid isolated from lipopolysaccharides of *Vibrio parahaemolyticus* O2 and O-untypable strain KX-V212, Carbohydr. Res. 338, 1055 (2003).
Hemeon, I., and Bennet, A.J., Sialic Acid and Structural Analogues: Stereoselective Syntheses, Synthesis 13, 1899 (2007).
Ishikawa, H., et al., High-Yielding Synthesis of the Anti-Influenza Neuramidase Inhibitor (–)-Oseltamivir by Three "One-Pot" Operations, Agnew. Chem. Int. Ed. 48, 1304 (2009).
Kajihara, Y., et al., Efficient Chemical Synthesis of CMP-NeuBAc and CMP-(NeuSAca2—L)NeuSAc, J. Org. Chem. 60, 5732 (1995).

(Continued)

*Primary Examiner* — Andrew D Kosar
*Assistant Examiner* — Raymond Covington
(74) *Attorney, Agent, or Firm* — Sonia Patenaude

(57) ABSTRACT

The present invention describes compounds of Formula I or a pharmaceutically acceptable salts or derivatives thereof. Compositions comprising compounds of Formula I are also described. The present invention further relates to a method of producing non-2-enonate compounds.

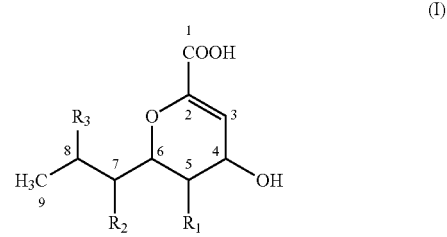

17 Claims, 6 Drawing Sheets

(56) References Cited

OTHER PUBLICATIONS

Karwaski, M-F., et al., High-level expression of recombinant *Neisseria* CMP-sialic acid synthetase in *Escherichia coli*, Protein Expr. Purif. 25, 237 (2002).

Kazeera, T.N., and Shevelev, A.B., Unknown Functions of Immunoglobulins A, Biochemistry (Mosc.) 72, 485 (2007).

Knirel, Y.A., et al., 5,7-Diamino-3,5,7,9-Tetradeoxynon-2-Ulosonic Acids in Bacterial Glycopolymers: Chemistry and Biochemistry, Adv. Carbohydr. Chem. Biochem. 58, 371 (2003).

Kooistra, O., et al., N-Methylation in polylegionaminic acid is associated with the phase-variable epitope of *Legionella pneumophila* serogroup 1 lipopolysaccharide Identi® cation of 5-(N,N-dimethylacetimidoyl)amino- and 5-acetimidoyl (N-methyl)amino-7-acetamido-3,5,7,9-tetradeoxynon-2-ulosonic acid in the O-chain polysaccharideEur. J. Biochem. 269, 560 (2002).

Lagoja, I.M., and Clercq, E.D., Anti-In£uenzaVirus Agents: Synthesis and Mode of Action, Med. Res. Reviews 28, 1 (2008).

Lehmann, F., et al., Sialic acid-specific lectins: occurrence, specificity and function, Cell. Mol. Life Sci. 63, 1331 (2006).

Li, X. et al., Structural and genetic characterization of the O-antigen of *Escherichia coli* O161 containing a derivative of a higher acidic diamino sugar, legionaminic acid, Carbohydr. Res. (2010).

Logan, S.M., et al., Structural heterogeneity of carbohydrate modifications affects serospecificity of *Campylobacter* flagellins, Mol. Microbiol. 46, 587 (2002).

Logan, S.M., et al., Identification of novel carbohydrate modifications on *Campylobacter jejuni* 11168 flagellin using metabolomics-based approaches, FEBS J. 276, 1014 (2009).

Logan, S.M., Flagellar glycosylation—a new component of the motility repertoire?, Microbiology 152, 1249 (2006).

Massiere, F., and Badet-Denisot, M-A., The mechanism of glutamine-dependent amidotransferases, Cell. Mol. Life Sci. 54, 205 (1998).

Mazumder, K., et al., Identification of a novel sugar 5,7-diacetamido-8-amino- 3,5,7,8,9-pentadeoxy-D-glycero-D-galacto-non-2-ulosonic acid present in the lipooligosaccharide of *Vibrio parahaemolyticus* O3:K6, Glycoconj. J. 25, 345 (2008).

McNally, D.J., et al., Targeted Metabolomics Analysis of *Campylobacter coli* VC167 Reveals Legionaminic Acid Derivatives as Novel Flagellar Glycans, J. Biol. Chem. 282, 14463 (2007).

Moscona, A., Neuraminidase Inhibitors for Influenza, N. Engl. J. Med. 353, 1363 (2005).

Potier, M., et al., Fluorometric Assay of Neuraminidase with a Sodium (4-Methylumbelliferyl-a-D-N-Acetylneuraminate) Substratel, Anal. Biochem. 94, 287 (1979).

Schirm, M., et al., Identification of Unusual Bacterial Glycosylation by Tandem Mass Spectrometry Analyses of Intact Proteins, Anal. Chem. 77, 7774 (2005).

Schoenhofen, I.C., et al., The CMP-legionaminic acid pathway in *Campylobacter*: Biosynthesis involving novel GDP-linked precursors, Glycobiology 19, 715 (2009).

Schoenhofen, I.C., et al., Elucidation of the CMP-pseudaminic acid pathway in *Helicobacter pylori*: synthesis from UDP-N-acetylglucosamine by a single enzymatic reaction, Glycobiology 16, 8C (2006a).

Schoenhofen, I.C., et al., Functional Characterization of Dehydratase/Aminotransferase Pairs from *Helicobacter* and *Campylobacter* Enzymes Distinguishing the Pseudaminic Acid and Bacillosamine Biosynthetic Pathways, J. Biol. Chem. 281, 723 (2006b).

Shashkov, A.S., et al., Structure of the O-antigen of *Providencia stuartii* O20, a new polysaccharide containing 5,7- diacetamido-3,5,7,9-tetradeoxy-L-glycero-D-galacto-non-2-ulosonic acid, Carbohydr. Res. 342, 653 (2007).

Soong, G., et al., Bacterial neuraminidase facilitates mucosal infection by participating in biofilm production, J. Clin. Invest. 116, 2297 (2006).

Thibault, P., et al., Identification of the Carbohydrate Moieties and Glycosylation Motifs in *Campylobacter jejuni* Flagellin, J. Biol. Chem. 276, 34862 (2001).

Twine, S.M., et al., Flagellar glycosylation in *Clostridium botulinum*, FEBS J. 275, 4428 (2008).

Varki, A., et al, editors. Essentials of Glycobiology. 2nd edition, Cold Spring Harbor (NY): Cold Spring Harbor Laboratory Press; 2009. Chapter 14.

Yamashita, M., et al., CS-8958, a Prodrug of the New Neuraminidase Inhibitor R-125489, Shows Long-Acting Anti-Influenza Virus Activity, Amtimicrobial Agents Chemotherapy 53, 186 (2009).

McNally, D. et al. "Functional characterization of the flagellar glycosylation locus in *Campylobacter jejuni* 81-176 using a focused metabolomics approach". Journal of Biological Chemistry, 2006, vol. 281, pp. 18489-18498.

\* cited by examiner

INHIBITORS OF SIALIDASE OR SIALIDASE-LIKE ENZYMES

CROSS-REFERENCE TO RELATED APPLICATIONS

This application is a national phase entry of International Patent Application PCT/CA2010/000680 filed May 4, 2010, which claims the benefit of United States Provisional Patent Application Serial No. 61/213,070 filed May 4, 2009.

FIELD OF THE INVENTION

The present invention relates to inhibitors of sialidase or sialidase-like enzymes. More specifically, the invention is directed to compounds for inhibition of sialidase or sialidase-like enzymes from virus, bacteria, or humans.

BACKGROUND OF THE INVENTION

The adhesion of pathogens to host cell surfaces is the initial and most critical step in their development of infection or disease. Several viral and bacterial families are known to utilize host sialic acid sugars for adherence or host-pathogen interactions (Lehmann et al, 2006). Sialic acid sugars are nonulosonic sugars, a family of nine-carbon α-keto acids. These molecules have been extensively investigated as drug targets.

However, there are currently a limited number of treatments available for viral and/or bacterial infections; unfortunately, many pathogens have developed resistance to the current medicines. Additionally, existing vaccination methods are not effective in guarding against all influenza virus infection, especially for newly emerging pandemic strains, as the coat of the virus changes continually and rapidly. These changes are predominantly found within surface epitopes of the abundant hemagglutinin (H) and neuraminidase (N) components, preventing their recognition by host antibodies. H and N are two large proteins on the viral particle surface that bind sialic acids of the host; the sialic acid binding activity of H mediates initial adherence to and entry into target cells, whereas N cleaves host sialic acids allowing the release of new progeny virus from infected cells, facilitating the invasion of other host cells (Moscona, 2005). The combination of various H and N components is the basis for classification of influenza A, with 16 H subtypes and 9 N subtypes identified so far. However, the sialic acid binding ability remains constant amongst all infective H and N variants formed through antigenic drift. In addition, many respiratory bacterial pathogens such as *Pseudomonas aeruginosa, Hemophilus influenzae* and *Streptococcus pneumoniae* produce neuraminidases (N). For the former, this N enzyme is required for biofilm formation and plays a key role in the initial stages of pulmonary infection, for example lung infections in cystic fibrosis patients (Soong et al., 2006).

Current antibiotics to treat influenza, such as Zanamivir and Oseltamivir, are sialic acid mimics that inhibit the function of N, thereby trapping progeny virus at the cell surface and limiting viral infection to one round of replication. They are rationally-designed synthetic derivatives, based on knowledge of the transition state of sialic acid and the 3-dimensional structure of N's binding pocket (Colman, 1994). However, the chemistries involved in producing these compounds are challenging, which presents a further obstacle in providing treatment (Ishikawa et al., 2009; Lagoja and Clercq, 2008).

As the threat of a global pandemic looms on the horizon, the development of more potent and effective pathogen inhibitors has gained in importance. However, compounds capable of treating or preventing pandemic disease remain elusive.

SUMMARY OF THE INVENTION

The present invention relates to inhibitors of sialidase or sialidase-like enzymes. More specifically, the invention is directed to compounds for inhibition of sialidase or sialidase-like enzymes from virus, bacteria, or humans.

In particular, the present invention provides compounds of Formula I

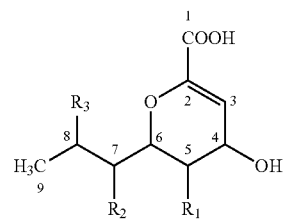

or a pharmaceutically acceptable salt or derivative thereof, wherein $R_1$ is NHAc, NHAm, NHAmNMe(a), NHAmNMe(b), NHAmNMe(c), NHAmNMe(d), NHAmdiNMe(a), NHPr2,3diOMe, NHPr, Glu, GluNMe, or NH4HB; $R_2$ is NHAc, NHAIa, NHAm, NHFo, NH3HB, (N-acetyl-D-alanyl)amido, or NHPr; and R3 is a hydroxyl or amino group (FIG. 1A).

In one embodiment of the present invention, the compound may be

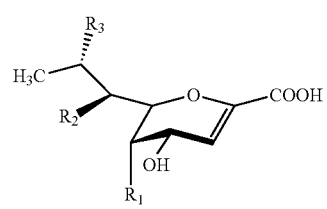

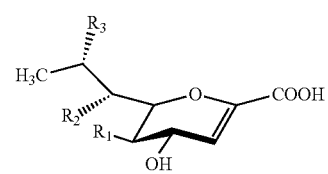

-continued

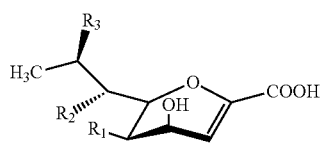

or

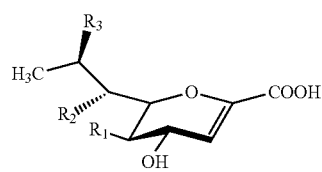

or a pharmaceutically acceptable salt or derivative thereof, wherein $R_1$, $R_2$ and $R_3$ are as defined for Formula I (FIGS. 1A and 1B).

The present invention encompasses bioreversible derivatives of the compounds of the present invention. The bioreversible derivative may be a C1-carboxylate ester of the compound of the present invention, wherein the ester comprises substituted or unsubstituted C1-C12.

The present invention further provides a composition comprising one or more than one compound of Formula I, and/or one or more than one bioreversible derivative of a compound of Formula I.

The present invention also provides a method of producing non-2-enonate compounds. The method may comprise the step of: heating a CMP-nonulosonate compound (a precursor), or a pharmaceutically acceptable salt or derivative thereof to a sufficient temperature and for a sufficient time so as to form the respective non-2-enonate (FIGS. 2 and 3). The nonulosonate may be a nonulosonate of human or bacterial origin. For example, the nonulosonate may be a sialic acid, or salt or derivative thereof; a pseudaminic acid, or salt or derivative thereof; or a legionaminic acid, or salt or derivative thereof.

In one embodiment, the method of the present invention may encompass a method of producing the compounds of the present invention (FIG. 2), comprising the step of:
  a) heating a compound of Formula VI

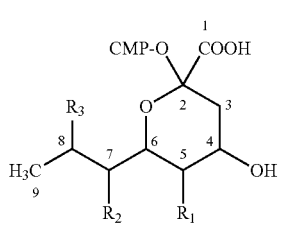

or a pharmaceutically acceptable salt or derivative thereof,
  to a sufficient temperature and
  for a sufficient time so as to form the compound of Formula I,
wherein $R_1$, $R_2$ and $R_3$ are as described for Formula I.

In another embodiment, the method of the present invention may encompass a method of producing a sialic acid non-2-enonate derivative (FIG. 3), comprising the step of:
  a) heating a compound of Formula VII

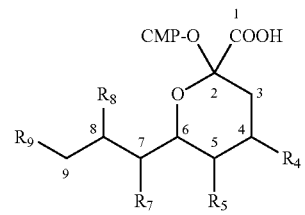

or a pharmaceutically acceptable salt or derivative thereof,
  to a sufficient temperature and for a sufficient time so as to form the sialic acid non-2-enonate derivative of formula VIII

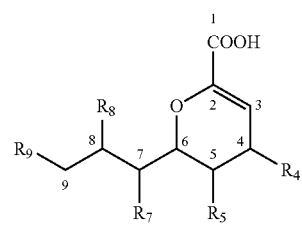

wherein
$R_4$ is selected from OH, O-acetyl, O-Fuc, O-Gal, or guanidino;
$R_5$ is selected from amino, N-acetyl, N-glycolyl, hydroxyl, N-acetimidoyl (acetamidino), N-glycolyl-O-acetyl, N-glycolyl-O-methyl, N-glycolyl-O-2-Neu5Gc, or N-azido-acetyl;
$R_7$ is selected from OH or O-acetyl;
$R_8$ is selected from OH, O-acetyl, O-methyl, O-sulfate, O-Sia, O-Glc, amino or azido; and
$R_9$ is selected from OH, O-acetyl, O-lactyl, O-phosphate, O-sulfate, O-Sia, amino or azido.

The methods as described above may optionally include a step of purifying the compounds.

The compounds of the present invention, and those used in the methods of the present invention, may be derived from natural compounds. As such, the present compounds may exhibit better potency in inhibiting sialidase or sialidase-like enzymes than those derived from rational design.

The present invention also provides a method of producing compound 3

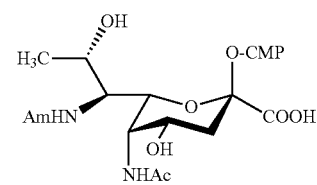

comprising contacting an enzyme of SEQ ID NO:1 with compound CMP-Pse5NHAc7NHAc under suitable conditions for the production of compound 3.

The present invention also provides a method of producing compound 7

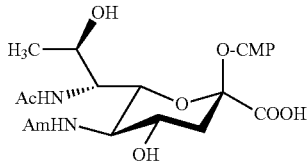

comprising contacting an enzyme of SEQ ID NO:4 with compound CMP-Leg5NHAc7NHAc under suitable conditions for the production of compound 7.

The present invention also provides a method of producing compound 9

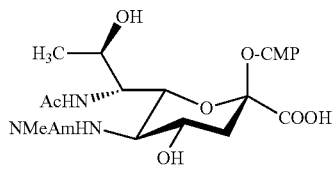

comprising contacting an enzyme of SEQ ID NO:7 with compound CMP-Leg5NHAm7NHAc under suitable conditions for the production of compound 9.

The present invention further provides a method of inhibiting sialidase or sialidase-like enzymes. The method may comprise the step of contacting the sialidase or sialidase-like enzyme with a compound of Formula I, or a composition comprising one or more than one compound of Formula I. The sialidase or sialidase-like enzymes may be of viral, bacterial, or human origin. For example, the compound of Formula I may be Leg5NHAc7NHAc 2-ene, Pse5NHAc7NHAc 2-ene, Leg5NHAm7NHAc 2-ene, or a combination thereof.

The present invention additionally provides a method of treating or preventing bacterial or viral infections. The method may comprise the step of administering one or more than one compound of Formula I, or a composition comprising one or more than one compound of Formula I to a subject in need thereof.

The present invention provides a facile and high-yielding process for producing non-2-enonate sugars. CMP-nonulosonate sugars, such as those precursors described above, may be heated in dry N,N'-dimethylformamide (DMF) resulting in mainly non-2-enonate sugar, CMP and non-reacted CMP-nonulosonate. Further purification is then simple, typically only requiring an ion-exchange chromatography step. Importantly, the non-reacted CMP-nonulosonate may be recovered, making the present process extremely efficient.

The present process has generated the production of novel non-2-enonate compounds derived from bacterial sialic acid-like sugars, such as compounds 2, 4, 6, 8 and 10. Thus, the family of bacterial sialic acid-like sugars may now be exploited to produce their respective novel non-2-enonate forms, which may then be evaluated for their ability to inhibit neuraminidase (or sialidase) enzymes. The CMP-activated forms of the bacterial sialic acid-like sugars could be subjected to the present process, producing the respective non-2-enonate forms. Furthermore, as the process of the present invention also functions with CMP-sialic acids (for example compound 11), non-2-enonate sialic acid-based compounds (for example, compound 12) may be prepared. Even without performing large-scale reactions, mg quantities of each non-2-enonate could be attained in near-pure quality. Each non-2-enonate derivative prepared in the Examples below was verified by exact-mass analysis (Table 8) with several being structurally characterized by NMR (Tables 4-7).

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein.

DETAILED DESCRIPTION OF THE INVENTION

The present invention relates to inhibitors of sialidase or sialidase-like enzymes. More specifically, the invention is directed to compounds for inhibition of sialidase or sialidase-like enzymes from virus, bacteria, or humans.

The challenge of developing or isolating more potent and effective pathogen inhibitors remains unmet, despite much activity in the area of sialic acid derivatives and/or mimics. The derivatives and mimics have been explored as potential disrupters of pathogen adherence and host-pathogen interaction via the sialic acid molecules present in the host.

In addition to sialic acid, two other structurally distinct nonulosonic sugars, pseudaminic (Pse; Schoenhofen et al., 2006a) and legionaminic (Leg; Schoenhofen et al., 2009) acid have been characterized. These sialic acid-like sugars are constituents of microbial glycans, and their structural similarity to sialic acid may render them effective sialic acid mimics. Currently, pseudaminic acid, legionaminic acid, and their derivatives can only be produced in sub-gram quantities, either by complex chemical and/or enzymatic synthesis in vitro or by isolation from natural resources.

The present invention provides non-2-enonate derivatives of bacterial sialic acid-like compounds, compounds of Formula I

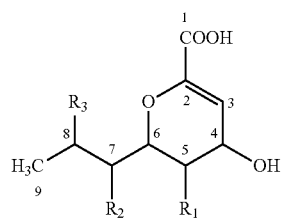

Figure 1A:
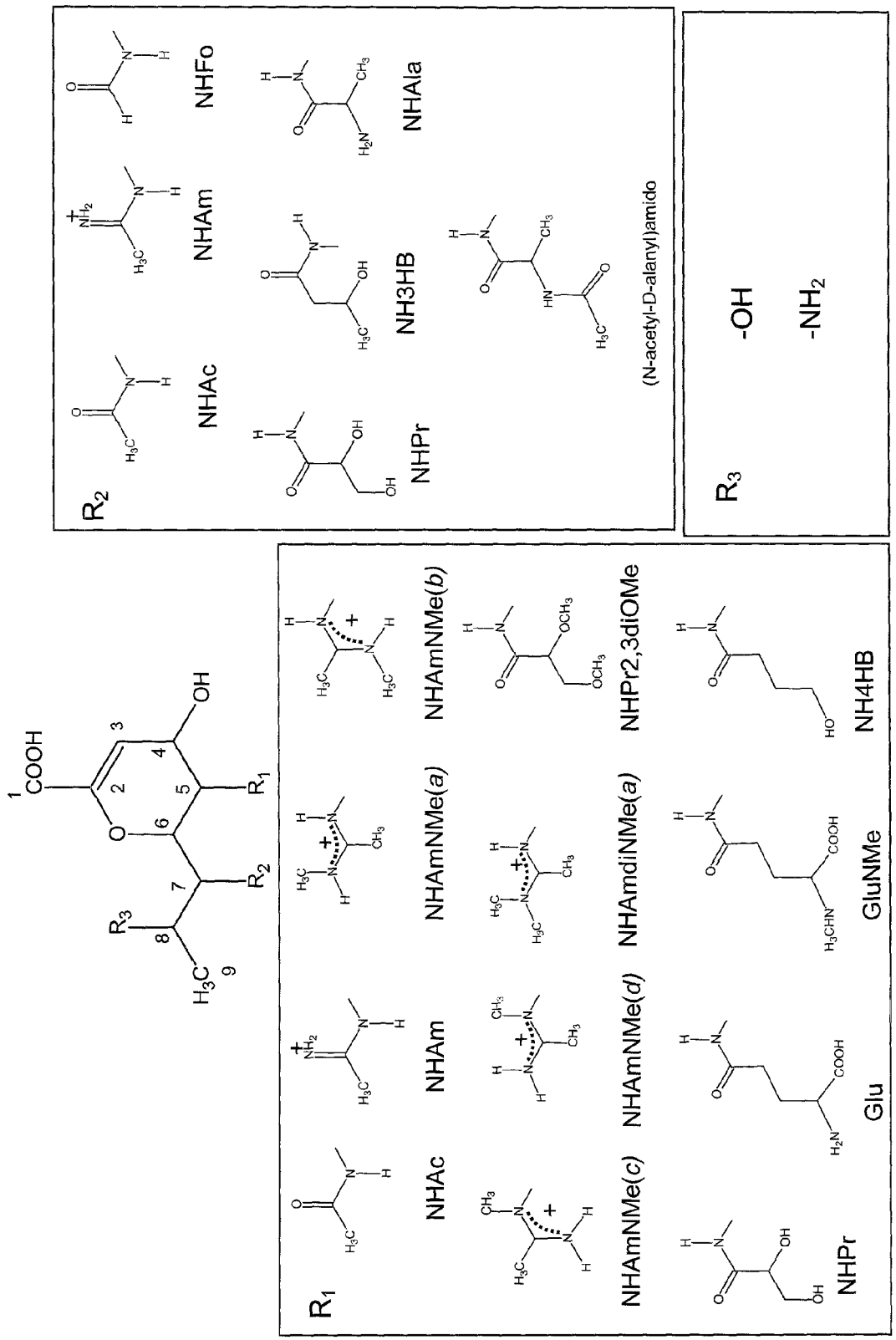
FIG. 1A shows the structure of the compound of Formula I and possible substituents. NHAc=acetamido; NHAla=N-(D-alanyl); NHAm=acetamidino; NHAmNMe=N-methyl-acetamidino; NHAmdiNMe=di-N-methyl-acetamidino; NHPr2,3diOMe=(2,3-di-O-methyl-propionoyl)amino; Glu=(glutam-4-yl)amino; GluNMe=(N-methyl-glutam-4-yl)amino; NH3HB=N—(R)-3-hydroxybutanoyl; NH4HB=N-4-hydroxybutanoyl; NHFo=N-formyl; NHPr=N-2,3-dihydroxypropionyl; (N-acetyl-D-alanyl)amido; $NH_2$=amino; OH=hydroxyl.

I or a pharmaceutically acceptable salt or derivative thereof, wherein $R_1$ is NHAc, NHAm, NHAmNMe(a), NHAmNMe(b), NHAmNMe(c), NHAmNMe(d), NHAmdiNMe(a), NHPr2,3diOMe, NHPr, Glu, GluNMe, or NH4HB; $R_2$ is NHAc, NHAla, NHAm, NHFo, NH3HB, (N-acetyl-D-alanyl)amido, or NHPr; and R3 is hydroxyl or amino group (FIG. 1A).

A person of skill in the art would recognize that a number of chiral centres are present in Formula I. The chiral centres may be in either configuration. For example, and without wishing to be limiting in any manner, in one embodiment of the present invention, the compound may be

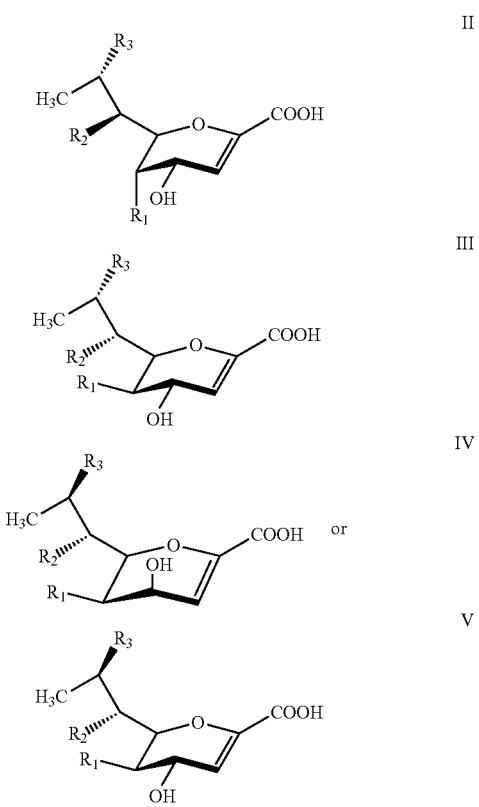

or a pharmaceutically acceptable salt or derivative thereof, wherein $R_1$, $R_2$, and $R_3$ are as defined for Formula I. Thus, when $R_3$ is OH (hydroxyl), then the compounds may be:
Formula II: 5-(R1)-7-(R2)-3,5,7,9-tetradeoxy-L-glycero-L-manno-non-2-enonate,
Formula III: 5-(R1)-7-(R2)-3,5,7,9-tetradeoxy-L-glycero-D-galacto-non-2-enonate,
Formula IV: 5-(R1)-7-(R2)-3,5,7,9-tetradeoxy-D-glycero-D-talo-non-2-enonate,
Formula V: 5-(R1)-7-(R2)-3,5,7,9-tetradeoxy-D-glycero-D-galacto-non-2-enonate.

Alternatively, when $R_3$ is $NH_2$ (amino), then the compounds may be:
Formula II: 5-(R1)-7-(R2)-8-amino-3,5,7,8,9-pentadeoxy-L-glycero-L-manno-non-2-enonate,
Formula III: 5-(R1)-7-(R2)-8-amino-3,5,7,8,9-pentadeoxy-L-glycero-D-galacto-non-2-enonate,
Formula IV: 5-(R1)-7-(R2)-8-amino-3,5,7,8,9-pentadeoxy-D-glycero-D-talo-non-2-enonate,
Formula V: 5-(R1)-7-(R2)-8-amino-3,5,7,8,9-pentadeoxy-D-glycero-D-galacto-non-2-enonate.

For example, and without wishing to be limiting in any manner, the compounds of the present invention may be, but are not limited to a compound of Formula II wherein $R_1$ is NHAc and $R_2$ is NHAc or NHAm. In another example, the compound may be, but are not limited to a compound of Formula V wherein $R_1$ is NHAc, NHAm, NHAmNMe(a), NHAmNMe(b), NHAmNMe(c), NHAmNMe(d), Glu, or GluNMe, and $R_2$ is NHAc.

In a specific, non-limiting example, the compounds of the present invention may be, but are not limited to:

5,7-diacetamido-3,5,7,9-tetradeoxy-L-glycero-L-manno-non-2-enonate (Pse5NHAc7NHAc g-ene);

5-acetamido-7-acetamidino-3,5,7,9-tetradeoxy-L-glycero-L-manno-non-2-enonate (Pse5NHAc7NHAm 2-ene);

5-(2,3-di-O-methyl-propionyl)amino-7-acetamido-3,5,7,9-tetradeoxy-L-glycero-L-manno-non-2-enonate (Pse5NHPr2,3diOMe7NHAc 2-ene);

5-(2,3-di-O-methyl-propionyl)amino-7-acetamidino-3,5,7,9-tetradeoxy-L-glycero-L-manno-non-2-enonate (Pse5NHPr2,3diOMe7NHAm 2-ene);

5,7-diacetamido-3,5,7,9-tetradeoxy-L-glycero-D-galacto-non-2-enonate (8eLeg5NHAc7NHAc 2-ene);

5-acetamido-7-N—(R)-3-hydroxybutanoyl-3,5,7,9-tetradeoxy-L-glycero-D-galacto-non-2-enonate (8eLeg5NHAc7NH3HB 2-ene);

5-acetamido-7-N-formyl-3,5,7,9-tetradeoxy-L-glycero-D-galacto-non-2-enonate (8eLeg5NHAc7NHFo 2-ene);

5,7-diacetamido-3,5,7,9-tetradeoxy-D-glycero-D-talo-non-2-enonate (4eLeg5NHAc7NHAc g-ene);

5-acetamidino-7-acetamido-3,5,7,9-tetradeoxy-D-glycero-D-talo-non-2-enonate (4eLeg5NHAm7NHAc 2-ene);

5-di-N-methyl-acetamidino-7-acetamido-3,5,7,9-tetradeoxy-D-glycero-D-talo-non-2-enonate (4eLeg5NHAmdiNMe7NHAc 2-ene);

5,7-diacetamido-8-amino-3,5,7,8,9-pentadeoxy-D-glycero-D-galacto-non-2-enonate (Leg5NHAc7NHAc8N 2-ene);

5,7-diacetamido-3,5,7,9-tetradeoxy-D-glycero-D-galacto-non-2-enonate (Leg5NHAc7NHAc g-ene);

5-acetamido-7-N-(D-alanyl)-3,5,7,9-tetradeoxy-D-glycero-D-galacto-non-2-enonate (Leg5NHAc7NHAIa 2-ene);

5-acetamidino-7-acetamido-3,5,7,9-tetradeoxy-D-glycero-D-galacto-non-2-enonate (Leg5NHAm7NHAc 2-ene);

5-N-methyl-acetamidino-7-acetamido-3,5,7,9-tetradeoxy-D-glycero-D-galacto-non-2-enonate (Leg5NHAmNMe7NHAc 2-ene);

5-di-N-methyl-acetamidino-7-acetamido-3,5,7,9-tetradeoxy-D-glycero-D-galacto-non-2-enonate (Leg5NHAmdiNMe7NHAc 2-ene);

5-(glutam-4-yl)amino-7-acetamido-3,5,7,9-tetradeoxy-D-glycero-D-galacto-non-2-enonate (Leg5Glu7NHAc 2-ene);

5-(N-methyl-glutam-4-yl)amino-7-acetamido-3,5,7,9-tetradeoxy-D-glycero-D-galacto-non-2-enonate (Leg5GluNMe7NHAc 2-ene);

or pharmaceutically acceptable salts or derivatives thereof.

The compounds of Formula I also encompass chemical derivatives of the compounds as described above. For example, the hydroxyl groups at C4 and/or the hydroxyl or amino groups at C8 may be derivatized by methods commonly used in the art. In a specific example, and not wishing to be limiting, the hydroxyl groups at C4 and/or C8 may be modified to O-acetyl; in another non-limiting example, the hydroxyl group at C8 can be modified such that it is O-linked to N-acetyl-glutamine. Chemical modifications of R group substituents are also encompassed by the present invention. These may include, but are not limited to modification of the $R_3$ amino group, the amino functionality of the N-(D-alanyl) [NHAIa] group, amino functionalities of the acetamidino [NHAm] groups, the amino functionality of the (glutam-4-yl)amino [Glu] group, the free amino group of the NHAm-NMe group, or the carboxyl functionality of (glutam-4-yl)amino [Glu] or (N-methyl-glutam-4-yl)amino [GluNMe] groups.

Pharmaceutically acceptable salts of the compounds of Formula I may include, but are not limited to acid or base addition salts derived from pharmaceutically acceptable inorganic and organic acids and bases; these salts may include, but are not limited to chlorides, sulfates, carbonates, phosphates, citrates, acetates, tartrate, carbonate, tannate, and stearate. Acid or base addition salts may be produced by reacting a compound of Formula I with an appropriate acid or base.

The present invention also encompasses bioreversible derivatives of the compounds of the present invention; these bioreversible derivatives may also be referred to as "prodrugs". By the term "bioreversible derivatives" or "prodrug", it is meant that the compounds of the present invention are presented as pharmacologically inert chemical derivatives; the bioreversible derivative is metabolized in vitro to the active molecule (i.e., the compounds of the present invention). The bioreversible derivatives may improve the physicochemical properties of the compounds of the present invention; for example, and without wishing to be limiting in any manner, the bioreversible derivatives may improve solubility, stability, and/or retention of the compounds of the present invention. The bioreversible derivative may be prepared using any bioreversible derivatizing technique known in the art (Yamashita et al. 2009). For example, and without wishing to be limiting in any manner, the bioreversible derivative may be obtained by conversion of the C1 carboxylate group of the compounds of the present invention to an ester; the ester may be a substituted or unsubstituted C1-C12 ester.

The compounds as described above may mimic the structure of sialic acid. Without wishing to be bound by theory, such compounds may inhibit the function of neuraminidase (N), thereby trapping progeny virus at the cell surface and limiting viral infection to one round of replication. Precursors to the compounds of the present invention were identified within, or on the surface of *Campylobacter, Legionella, Clostridium, Providencia, Helicobacter, Pseudomonas, Vibrio*, and other species (Li et al., 2010; Beynon et al., 1994; Shashkov et al., 2007; Mazumder et al., 2008; Knirel et al., 2003; Schoenhofen et al., 2006a, 2009; McNally et al., 2007; Logan et al., 2002, 2006, 2009; Kooistra et al., 2002; Thibault et al., 2001; Twine et al., 2008; Hashii et al., 2003; Schirm et al, 2005). For example, there are hundreds of thousands of proteins making up the flagella of *Campylobacter* species, and each of these proteins may contain up to 19 unique sialic acid-like sugars, the result being that the entire filament is coated with these sugars (Thibault et al., 2001; McNally et al., 2007). As the compounds of the present invention are derived from these natural products, they may exhibit far more potency as inhibitors of influenza, viruses in general, or bacteria than those resulting from rational drug design.

The ability to bind sialic acid remains constant amongst all infective H and N variants formed through antigenic drift. In fact, it has been shown that mutations found within the sialic acid binding pocket of N significantly attenuated virulence (Gubareva et al, 2000). As sialic acid binding of H and N is critical to the virulence of influenza, the development of resistance to the compounds of the present invention would likely result in non-infective virus, as changes to the active sites of H and N would prevent their normal role of binding sialic acid. Thus, the antigenic drift normally observed, which changes the surface epitopes of influenza, would not prevent the inhibition by the compounds of the present invention.

The present invention further provides compositions, also referred to herein as "formulations", comprising the compounds of the present invention, bioreversible derivatives thereof, or a combination thereof. In addition to the compounds of the present invention, the compositions may comprise a pharmaceutically acceptable carrier, diluent or excipient (or “pharmacologically acceptable ingredient”). The carrier, diluent or excipient may be any suitable carrier, and must be compatible with other ingredients in the composition, and with the method of delivery of the composition. The composition may be in any suitable form; for example, the composition may be provided in liquid form, suspension form, powder form (for example, lyophilised), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH. In a specific, non-limiting example, the pharmaceutically acceptable carrier may be saline. Dry powders may also include additives to improve stability and/or carriers to increase bulk/volume; for example, and without wishing to be limiting, the dry powder composition may comprise sucrose or trehalose. It would be within the competency of a person of skill in the art to prepare suitable compositions comprising the present compounds.

For example, and without wishing to be limiting in any manner, pharmacologically acceptable ingredients for nutraceutical and/or pharmaceutical compositions, include antiadherents, binders (e.g. starches, sugars, cellulose, hydroxypropyl cellulose, ethyl cellulose, lactose, xylitol, sorbitol and maltitol), coatings (e.g. cellulose, synthetic polymers, corn protein zein and other polysaccharides), disintegrants (e.g. starch, cellulose, cross-linked polyvinyl pyrrolidone, sodium starch glycolate and sodium carboxymethyl cellulose), fillers/diluents (e.g. water, plant cellulose, dibasic calcium phosphate, vegetable fats and oils, lactose, sucrose, glucose, mannitol, sorbitol and calcium carbonate), flavors and colors, glidants, lubricants (e.g. talc, silica, vegetable stearin, magnesium stearate and stearic acid), preservatives (e.g. vitamin A, vitamin E, vitamin C, selenium, cysteine, methionine, citric acid, sodium citrate, methyl paraben and propyl paraben), antioxidants, sorbents, sweeteners, and mixtures thereof.

The formulations of the present invention may comprise one or more than one of the compounds of the present invention; in particular, and without wishing to be limiting in any manner, the present invention encompasses a composition comprising a mixture (or “cocktail”) of the compounds of the present invention. Such a mixture may provide a composition with increased potency and may prevent the development of resistance.

The compounds of the present invention, or compositions comprising the compounds, may be used for the treatment or prophylaxis of bacterial or viral infections. Because the compounds of the present invention mimic sialic acid and are naturally-derived, they may exhibit improved potency over rationally designed drugs. The compounds of the present invention may inhibit the function of neuraminidase (N), thereby trapping progeny virus at the cell surface and limiting viral infection to one round of replication. The compounds may also inhibit human sialidases or neuraminidases, and may be used to modify biological activity for human disease treatment purposes.

The formulations of the present invention may be delivered by any suitable route of administration known in the art. For example, and without wishing to be limiting, the formulations may be delivered intra-nasally or orally. In a non-limiting example, the compositions of the present invention are applied intra-nasally.

The compounds and compositions of the present invention may be administered in a suitable amount or dosage form. As would be recognized by one of skill in the art, the particular amount or dosage will vary based on the specific compound, the route of administration, the infection being treated, and the specifics of the patient. However, a suitable amount or dosage may be, but is not limited to the range of about 0.01 to 750 mg/kg of bodyweight per day; for example, the suitable amount may be 0.01, 0.05, 0.1, 0.5, 1, 5, 10, 50, 100, 150, 200, 250, 300, 350, 400, 450, or 500 mg/kg of bodyweight per day, or any amount there between.

The present invention further provides a method of producing non-2-enonate derivatives of nonulosonate sugars. Nonulosonate sugars, also referred to herein as “nonulosonic acid”, are nine-carbon $\alpha$-keto acids, and may include but are not limited to sialic acid, pseudaminic acid, and legionaminic acid. The method may comprise the step of: heating a CMP-nonulosonate derivative compound (a precursor), or a pharmaceutically acceptable salt or derivative thereof to a sufficient temperature and for a sufficient time so as to form the non-2-enonate derivative. The nonulosonate derivative may be a nonulosonate of human or bacterial origin. For example, the nonulosonate derivative may be a sialic acid derivative, or salt or derivative thereof; a pseudaminic acid derivative, or salt or derivative thereof; or a legionaminic acid derivative, or salt or derivative thereof.

The present invention also encompasses a method of producing a compound of Formula I. The method may comprise the steps of a) heating a compound of Formula VI

VI 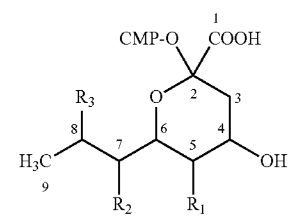 or a pharmaceutically acceptable salt or derivative thereof, to a sufficient temperature and for a sufficient time so as to form the compound of Formula I, wherein $R_1$, $R_2$, and $R_3$ are the same as those described for the compound of Formula I.

In another embodiment, the method of the present invention may encompass a method of producing a sialic acid derivative of Formula VIII, comprising the step of:

a) heating a compound of Formula VII

VII 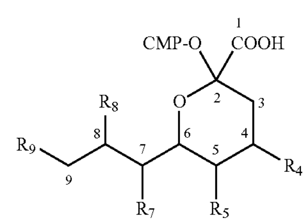 or a pharmaceutically acceptable salt or derivative thereof, to a sufficient temperature and for a sufficient time so as to form the sialic acid non-2-enonate derivative of Formula VIII, wherein $R_4$ is selected from OH, O-acetyl, O-Fuc, O-Gal, or guanidino;

R$_5$ is selected from amino, N-acetyl, N-glycolyl, hydroxyl, N-acetimidoyl (acetamidino), N-glycolyl-O-acetyl, N-glycolyl-O-methyl, N-glycolyl-O-2-Neu5Gc, N-azidoacetyl;

R$_7$ is selected from OH or O-acetyl;

R$_8$ is selected from OH, O-acetyl, O-methyl, O-sulfate, O-Sia, O-Glc, amino or azido; and R$_9$ is selected from OH, O-acetyl, O-lactyl, O-phosphate, O-sulfate, O-Sia, amino or azido.

The precursor compounds (Formula VI and VII) may be obtained using enzymatic and/or chemical synthesis steps, starting from compounds of Formula IX and X, respectively.

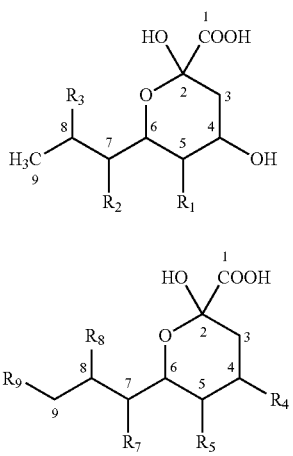

Figure 3:
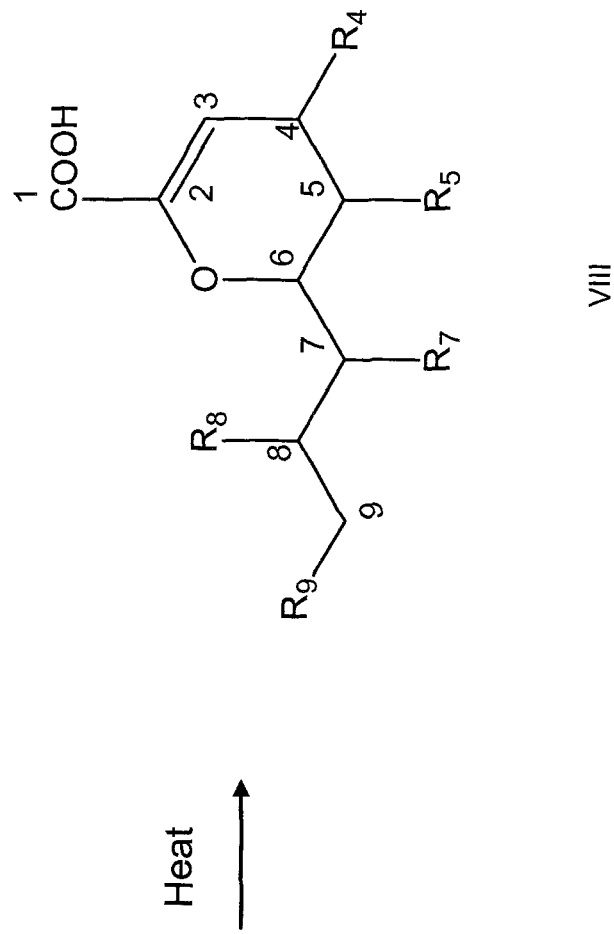
FIG. 3 shows a schematic of the method for preparing sialic acid non-2-enonate derivatives. The precursors (Formula VII) used in the method include a cytidine 5'-monophosphate (CMP) moiety, which may be produced using a combination of enzymatic and chemical synthesis steps. R4=OH, O-acetyl, O-Fuc, O-Gal, or guanidino; R5=amino, N-acetyl, N-glycolyl, hydroxyl, N-acetimidoyl (acetamidino), N-glycolyl-O-acetyl, N-glycolyl-O-methyl, N-glycolyl-O-2-Neu5Gc, or N-azido-acetyl; R7=OH or O-acetyl; R8=OH, O-acetyl, O-methyl, O-sulfate, O-Sia, O-Glc, amino, or azido; R9=OH, O-acetyl, O-lactyl, O-phosphate, O-sulfate, O-Sia, amino, or azido.
Figure 3:
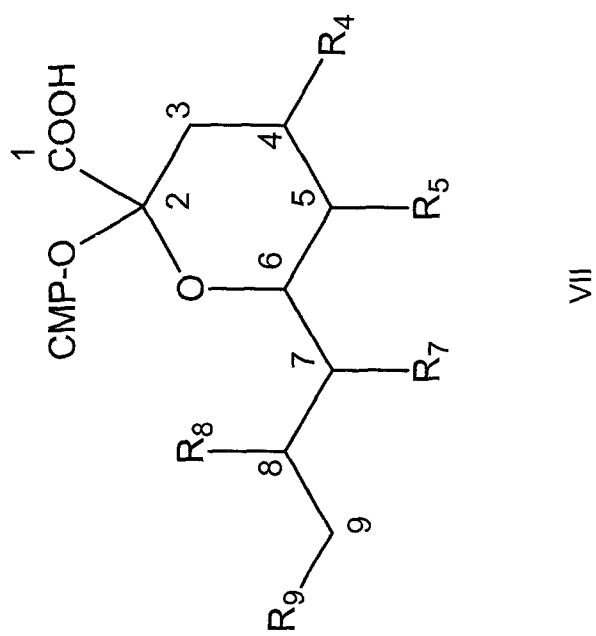

The compounds of Formula IX and X may be naturally-occurring compounds (Li et al., 2010; Beynon et al., 1994; Shashkov et al., 2007; Mazumder et al., 2008; Knirel et al., 2003; Schoenhofen et al., 2006a, 2009; McNally et al., 2007; Logan et al., 2002, 2006, 2009; Kooistra et al., 2002; Thibault et al., 2001; Twine et al., 2008; Hashii et al., 2003; Schirm et al, 2005), and/or may be purchased, synthesized, or isolated using methods known in the art (Hemeon and Bennet, 2007). In order to prepare the precursor compounds of Formula VI, the compounds of Formula IX are conjugated to cytidine 5'-monophosphate (CMP) by enzymatic reaction, wherein R$_1$, R$_2$ and R$_3$ are the same as those described for the compound of Formula I; similarly, to prepare the precursor compounds of Formula VII, the compounds of Formula X are conjugated to cytidine 5'-monophosphate (CMP) by enzymatic reaction, wherein the R groups are the same as those described for the compound of Formula VIII (FIG. 3). For example, and without wishing to be limiting, the precursor compound may be prepared by the methods, or by slightly modified methods, described by Schoenhofen et al. (2006a, 2009), International Application No. PCT/CA2009/001800, filed Dec. 16, 2009, or U.S. Provisional Application Ser. No. 61/326,015. Alternatively, the compounds of Formula VI or VII may be prepared by chemical conjugation of CMP to a compound of Formula IX or X, respectively, for example, as described by Kajihara et at (1995).

In the methods as described above, the "sufficient temperature" may be any temperature in the range of about 37° C. to about 110° C.; for example, and without wishing to be limiting, the temperature may be about 37, 38, 39, 40, 45, 50, 55, 60, 65, 70, 75, 80, 85, 90, 95, 100, 105 or 110° C., or any temperature there between, or any range of temperatures within the temperatures just defined. In a specific, non-limiting example, the sufficient temperature may be about 95, 100, or 105° C., or any temperature there between.

The "sufficient time" in the methods described above may be any time within the range of about 0.1 minutes to about 60 minutes, or about 1 hour to about 24 hours; for example, and without wishing to be limiting, the time may be about 0.1, 0.5, 1, 2, 3, 4, 5, 10, 15, 20, 25, 30, 35, 40, 45, 50, 55, 60, minutes, or 1, 2, 3, 4, 5, 6, 7, 8, 9, 10, 12, 13, 14, 15, 16, 17, 18, 19, 20, 21, 22, 23, or 24 hours, or any time therebetween, or any range of times within the times just defined. In a specific, non-limiting example, the sufficient time may be 15 or 20 minutes, or may be 6 hours.

The reaction may occur in any suitable organic or aqueous environment. For example, the reaction may occur in N,N'-dimethylformamide (DMF), water, saline, a suitable buffer, or buffered saline.

The methods as described above may further comprise a further step of purifying the compounds of Formula I. The purification of the compounds of the present invention may be done in any suitable manner known in the art. For example, and without wishing to be limiting, the compounds may be purified by chromatography, precipitation or re-crystallization, or any other suitable method. For example, by removing precipitate from reactions and/or subjecting reactions to anion-exchange chromatography (for example, by MonoQ 4.6/100 PE, GE Healthcare, or other suitable apparatus) using ammonium bicarbonate buffer.

The present invention also provides a method of producing compound 3

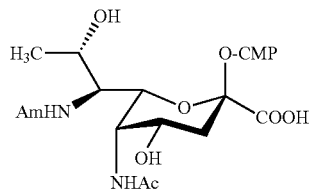

comprising contacting an enzyme of SEQ ID NO:1 with compound CMP-Pse5NHAc7NHAc under suitable conditions for the production of compound 3. Those of skill in the art would be familiar with conditions suitable for the present reaction.

The present invention also provides a method of producing compound 7

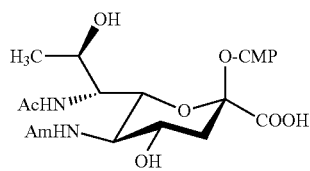

comprising contacting an enzyme of SEQ ID NO:4 with compound CMP-Leg5NHAc7NHAc under suitable conditions for the production of compound 7. Those of skill in the art would be familiar with conditions suitable for the present reaction.

The present invention also provides a method of producing compound 9

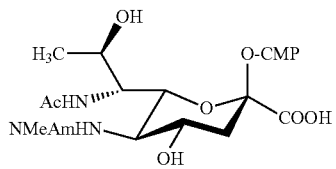

comprising contacting an enzyme of SEQ ID NO:7 with compound CMP-Leg5NHAm7NHAc under suitable conditions for the production of compound 9. Those of skill in the art would be familiar with conditions suitable for the present reaction.

The present invention further provides a method of inhibiting sialidase or sialidase-like enzymes, comprising contacting the sialidase or sialidase-like enzyme with an effective amount of the compound of Formula I, or a composition comprising one or more than one compound of Formula I. By the term sialidase, also referred to herein as "neuraminidase", it is meant a protein on the viral particle surface that binds sialic acids of the host; sialidase or neuraminidase cleaves host sialic acids allowing the release of new progeny virus from infected cells, facilitating the invasion of other host cells (Moscona, 2005). Sialic acid mimics may inhibit the function of N, thereby trapping progeny virus at the cell surface and limiting viral infection to one round of replication. By the term sialidase-like enzyme, it is meant an enzyme that shows activity similar to neuraminidase, i.e., that cleaves sialic acids. The sialidase or sialidase-like enzymes may be of viral, bacterial, or human origin. Without wishing to be bound by theory, contacting the sialidase or sialidase-like enzyme with a compound encompassed by the present invention prevents its action on sialic acid molecules. The compound of Formula I may be Leg5NHAc7NHAc 2-ene, Pse5NHAc7NHAc 2-ene, Leg5NHAm7NHAc 2-ene, or a combination thereof.

The present invention additionally provides a method of treating or preventing bacterial or viral infections. The method may comprise the step of administering an effective amount of one or more than one compound of Formula I, or a composition comprising one or more than one compound of Formula I to a subject in need thereof.

By the term "effective amount" in the methods as described above, it is meant an amount to provide sialidase or sialidase-like enzyme-inhibiting effect. Without wishing to be bound by theory, this in turn may provide treatment of or prevention from bacterial or viral infections. An effective amount is often based on the weight of the subject to whom it is administered, and may be easily determined by those of skill in the art.

The process for producing non-2-enonate sugars described herein is facile and high-yielding. CMP-nonulosonate sugars, such as those precursors described above, may be heated in dry N,N'-dimethylformamide (DMF) resulting in mainly non-2-enonate sugar, CMP and non-reacted CMP-nonulosonate. Further purification is then simple, typically only requiring an ion-exchange chromatography step. Importantly, the non-reacted CMP-nonulosonate may be recovered, making the present process extremely efficient.

Figure 1B:
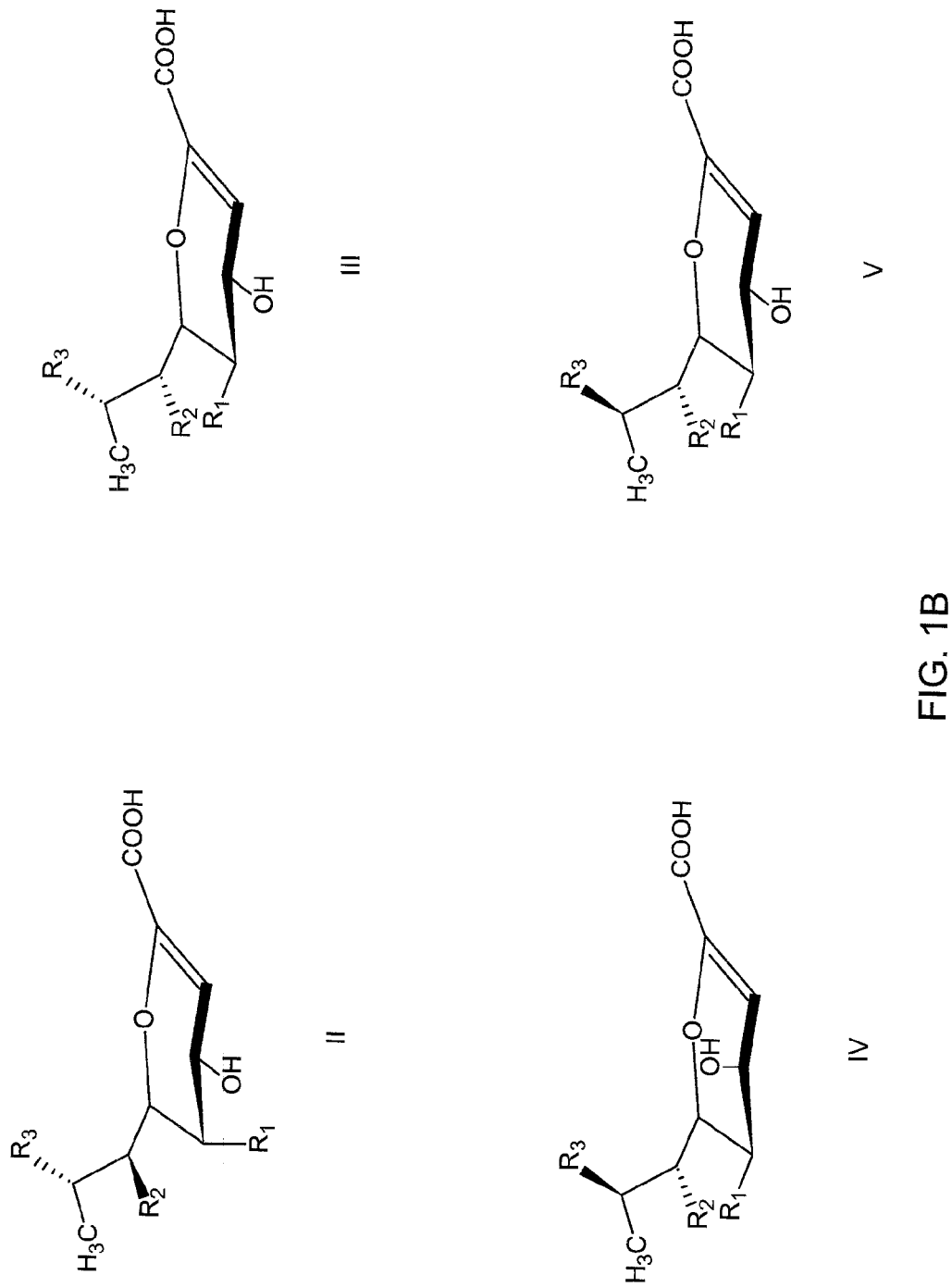
FIG. 1B shows preferred embodiments of the compounds of the present invention. When $R_3$ is OH (hydroxyl), then Formula II: 5-(R1)-7-(R2)-3,5,7,9-tetradeoxy-L-glycero-L-manno-non-2-enonate, Formula III: 5-(R1)-7-(R2)-3,5,7,9-tetradeoxy-L-glycero-D-galacto-non-2-enonate, Formula IV: 5-(R1)-7-(R2)-3,5,7,9-tetradeoxy-D-glycero-D-talo-non-2-enonate, Formula V: 5-(R1)-7-(R2)-3,5,7,9-tetradeoxy-D-glycero-D-galacto-non-2-enonate. When $R_3$ is $NH_2$ (amino), then Formula II: 5-(R1)-7-(R2)-8-amino-3,5,7,8,9-pentadeoxy-L-glycero-L-manno-non-2-enonate, Formula 5-(R1)-7-(R2)-8-amino-3,5,7,8,9-pentadeoxy-L-glycero-D-galacto-non-2-enonate, Formula IV: 5-(R1)-7-(R2)-8-amino-3,5,7,8,9-pentadeoxy-D-glycero-D-talo-non-2-enonate, Formula V: 5-(R1)-7-(R2)-8-amino-3,5,7,8,9-pentadeoxy-D-glycero-D-galacto-non-2-enonate. $R_1$ and $R_2$ are as defined in FIG. 1A.
Figure 2:
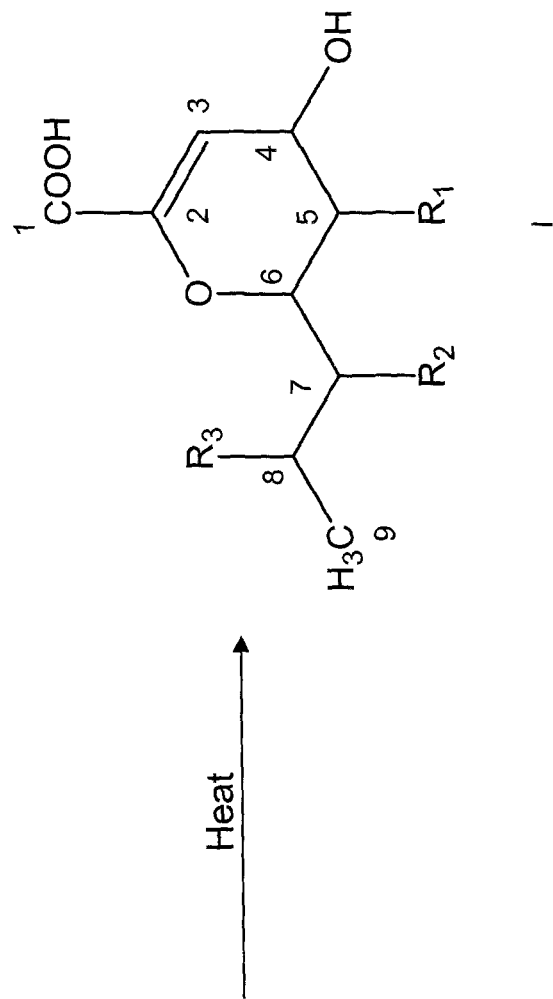
FIG. 2 shows a schematic of the method for preparing derivatives of bacterial sialic acid-like non-2-enonate compounds of the present invention. The precursor of the compounds of Formula VI include a cytidine 5'-monophosphate (CMP) moiety. These precursors may be produced using a combination of enzymatic and chemical synthesis steps.
Figure 2:
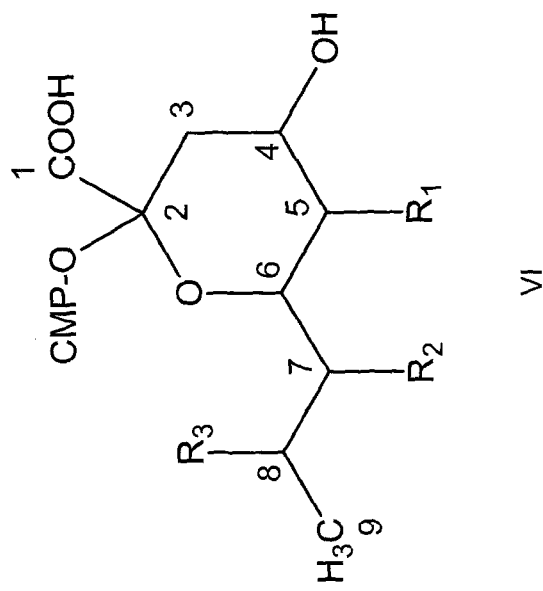

Therefore, the process of the present invention may facilitate the preparation of a highly diverse library of non-2-enonate sugars, in which the only limiting factor is the abundance of novel CMP-nonulosonate derivatives (FIGS. 1-3). Importantly, the present process has generated the production of novel non-2-enonate compounds derived from bacterial sialic acid-like sugars, such as compounds 2, 4, 6, 8 and 10. Thus, the family of bacterial sialic acid-like sugars may now be exploited to produce their respective novel non-2-enonate forms, which may then be evaluated for their ability to inhibit neuraminidase (or sialidase) enzymes. The CMP-activated forms of the bacterial sialic acid-like sugars could be subjected to the present process, producing the respective non-2-enonate forms. The bacterial sialic acid-like sugars may be, but is not limited to those which have been previously identified (for example, see Li et al., 2010; Beynon et al., 1994; Shashkov et al., 2007; Mazumder et al., 2008; Knirel et al., 2003; Schoenhofen et al., 2006a, 2009; McNally et al., 2007; Logan et al., 2002, 2006, 2009; Kooistra et al., 2002; Thibault et al., 2001; Twine et al., 2008; Hashii et al., 2003; Schirm et al, 2005), naturally-derived sugars, or may be synthetic derivatives thereof.

Furthermore, as the process of the present invention also functions with CMP-sialic acids (for example compound 11), non-2-enonate sialic acid-based compounds (for example, compound 12) may be prepared. Moreover, this process may be utilized for the cost-effective production of current antivirals such as zanamivir (a 4-guanidino derivative of compound 12), the difference between in production being the presence of a 4-guanidino CMP-sialic acid derivative (in the production of zanamivir). Interestingly, the conversion of CMP-legionaminic acid derivatives (D-glycero-D-galacto configuration) to corresponding non-2-enonate sugars was higher than that observed for CMP-pseudaminic acid derivatives (L-glycero-L-manno configuration), which suggests a possible influence of stereochemistry (approximately 90% and 35% conversion, respectively). Without performing large-scale reactions, mg quantities of each non-2-enonate could be attained in near-pure quality using the process of the present invention. Each non-2-enonate derivative prepared in the Examples below was verified by exact-mass analysis (Table 8) with several being structurally characterized by NMR (Tables 4-7).

The present invention will be further illustrated in the following examples. However, it is to be understood that these examples are for illustrative purposes only and should not be used to limit the scope of the present invention in any manner.

Example 1

Enzyme Production

Enzymes were prepared for production of CMP-nonulosonate precursors to specific compounds of the present invention. Plasmid DNA construction and sequencing were similar to previously described methods (Schoenhofen et al., 2006a; 2006b; 2009).

a. PseA Enzyme: a Nucleotide Sequence Encoding the Sequence (SEQ ID NO: 1)
MGSSHHHHHHGSMKFCKKCVMPDTKPDLHFDEEGVCDACRSQEAKNQNIN

WQEREKEFFELIKKYKKHPVYDCVIGVSGGKDSTFQVVKMLELGLNPLCV

CFEPSVPTKIGRKNLDNLNHLGVDLIHIKRDPKVYQKLAREAFIRTGDNE

WQNHLGIFTSVPRIAVNFGVPLIIWGESPQIEYGGPASSKNKNILGREWL

EEFGGLLGNRASDMLGVNGITEKDLFLYTYPSDEELQRVGVTGLFLGYYF

KWDYKKILEISKKYGFLTLDHPVETTYENFENLDCYSNHVHDYLKYCKYG

-continued

FGRATDNACLDIRLGYISREEGVRLAQKYDGKPPKKAIKKYLEFSGFSEE

EFQKIVDSFTNKKIFKRDENGKFIRDYDGSLVRKDECVLK, an enzyme based on PseA (Cj1316c), was cloned into plasmid pFO4 (as described by Schoenhofen et al., 2006b) using oligonucleotides (SEQ ID NO: 2)
NRC64 5'-GGATCCATGAAATTTTGTAAAAAATGTGTGATGCCAG-3'
and (SEQ ID NO: 3)
NRC65 5'-CTCGAGTCATTTTAAAACACACTCGTCTTTTCTTACC-3'.

The resulting plasmid, pNRC39.1, was transformed by electroporation into electro-competent Top10F' or DH10B (Invitrogen) *Escherichia coli* cells for cloning purposes, and were sequenced as described previously (Schoenhofen et al., 2006a; 2006b; 2009). The vector was introduced into BL21[DE3] (Novagen) *E. coli* cells for Cj1316c protein production b. LegA Enzyme: a Nucleotide Sequence Encoding the Sequence (SEQ ID NO: 4)
MGSSHHHHHHGSMIYCDHCVMPNTRPGINFTKDKEGKNICSACINHKNKE

NIDYKARFKELEVLCDKYRRMNGKFEYDCAIAVSGGKDSHFQVHIMKEKL

GMNPILFSVEDNFTMTEAGKKNLKNLSETFGCHIISLKPDIKTQKKVMLK

TFEKYGKPTWFIDRLIYSYPFAMALKFNTPLLVYGENVSYEYGGSDTEET

PSAKEIFLNGVASDLNINEFIDDEIKEENLQLFFNPNKDKLDKLNPIYLS

YFVKWNSYSNYIFAKSRGFTDLEGEWDRTMCAENFDQVDSIGYILHAWMK

YPKFGHACASDYAARFVRYGLLSRKEAIELVQKRDHKLDNKCVEDFCNFI

GISKTTFWKIVEKHYNMDLFYKNDFGEFKLKNKLQ, an enzyme based on PtmG (Cj1324), was cloned into plasmid pFO4 (as described by Schoenhofen et al., 2006b) using oligonucleotides NRC-97
(SEQ ID NO: 5)
5'-GGATCCATGATTTATTGTGATCACTGCGTG-3'
and

NRC98
(SEQ ID NO: 6)
5'-CTCGAGTTATTGTAATTTGTTTTTTAATTTAAATTCTCC-3'.

The resulting plasmid, pNRC50.2, was transformed by electroporation into electro-competent Top10F' or DH10B (Invitrogen) *Escherichia coli* cells for cloning purposes, and were sequenced as described previously (Schoenhofen et al., 2006a; 2006b; 2009). The vector was introduced into BL21-CodonPlus[DE3]-RIL (Novagen) *E. coli* cells for Cj1324 protein production.

c. LegM Enzyme: a Nucleotide Sequence Encoding the Sequence (SEQ ID NO: 7)
MGSSHHHHHHGSQNSLEAYTMKYNENGYGLLFPDGHVVRFYERILKYKLN

KINGNLLDFGCGNGVHSAYFQSKGFKTFGIDIVPSLKEIWEQNISGGGYC

KIIEPNSSIKGLFDENMDIIFANQSLYYIPLKELKQNILEFYELLNTGGI

LFATMMSKKNYYFSHSQKEEKNGLSKVEINGRLNETSFIHFIDKAEDLEN

LFQPFETLFLGDYDPINFYNFEGSAHHYIYIGIKK, an enzyme based on PtmH (Cj1325/26), was cloned into plasmid pFO4 (as described by Schoenhofen et al., 2006b) using oligonucleotides NRC308
(SEQ ID NO: 8)
5'-GGATCCCAAAACTCATTAGAAGCTTATACAATGAAATATAATG-3'
and

NRC309
(SEQ ID NO: 9)
5'-GAATTCTTATTTTTTAATACCTATATAAATATAATGGTGTGCCG-3'.

GenBank annotates the ORFs Cj1325 and Cj1326 separately, although this was found to be one contiguous ORF, referred to herein as Cj1325/26. The separate annotation may be due to the presence of a poly G tract between Cj1325 and Cj1326. Initial cloned plasmids contained 10 G's within this region, which disrupted the reading frame and prevented expression of full-length enzyme. As such, site-directed mutagenesis using oligonucleotides

1325/26-F
(SEQ ID NO: 10)
5'-GAAATTTGGGAGCAAAATATTAGCGGAGGAGGATATTGTAAAATTAT

AGAACCAAATTC-3'

1325/26-R
(SEQ ID NO: 11)
5'-GAATTTGGTTCTATAATTTTACAATATCCTCCTCCGCTAATATTTTG

CTCCCAAATTTC-3' was performed using the QuikChange II mutagenesis kit (Stratagene) according to the manufacturer's instructions to disrupt the poly G tract. The resulting plasmid, designated pNRC180.6, had the sequence GGAG-GAGGA in this region and allowed full-length protein (SEQ ID NO:7) production. The plasmid was transformed by electroporation into electro-competent Top10F' or DH10B (Invitrogen) *Escherichia coli* cells for cloning purposes, and were sequenced as described previously (Schoenhofen et al., 2006a; 2006b; 2009). The vector was introduced into BL21-CodonPlus[DE3]-RIL (Novagen) *E. coli* cells for Cj1325/26 protein production.

Protein expression: *E. coli* strains used for protein expression were either those prepared in a-c above, or those described by Schoenhofen et al. (2006a; 2006b; 2009), such as pNRC8.1, which encodes HP0840His$_6$; pNRC37.1, which encodes His$_6$HP0366; pNRC129.2, which encodes His$_6$HP0327; pNRC131.1, which encodes HP0326BHis$_6$; pNRC36.3, which encodes His$_6$HP0178; pNRC38.1, which encodes His$_6$HP0326A; pNRC16.1, which encodes Cj1319His$_6$; pNRC83.1, which encodes His$_6$Cj1320; pNRC164.3, which encodes His$_6$Cj1298; pNRC134.1, which encodes His$_6$Cj1328; pNRC51.1, which encodes His$_6$Cj1327; and pNRC139.1, which encodes Cj1331His$_6$. Briefly, each expression strain was grown in 1 to 2 l of 2× yeast tryptone (Schoenhofen et al., 2006b), depending on expression level, with either kanamycin (50 µg ml$^{-1}$), ampicillin (75 µml$^{-1}$) or ampicillin and chloramphenicol (75 µg ml$^{-1}$ and 40 µg ml$^{-1}$) for selection. The cultures were grown at 30° C., induced at an OD$_{600}$ of 0.6 with 0.1 mM isopropyl-1-thio-β-D-galactopyranoside, and harvested 2.75 h later. In general, cell pellets were re-suspended in lysis buffer (50 mM sodium phosphate, 400 mM NaCl, 10 mM β-mercaptoethanol) containing 10 mM imidazole and complete protease inhibitor mixture, EDTA-free (Roche Applied Science). After addition of 10 µg ml$^{-1}$ of DNaseI (Roche Applied Science), the cells were disrupted by two passes through an emulsiflex C5 (20,000 psi). Lysates were centrifuged at 100,000×g for 50 min at 4° C., and the supernatant fraction was applied to a 2 ml nickel-nitrilotriacetic acid (Qiagen) column equilibrated in 10 mM imidazole lysis buffer, using a flow rate of 1 ml min$^{-1}$. After sample application, the column was washed with 10 column volumes of 10 mM imidazole lysis buffer. To elute the protein of interest, a linear gradient from 10 to 100 mM imidazole, in lysis buffer, over 25 column volumes was applied to the column prior to a final pulse of 20 column volumes of 200 mM imidazole lysis buffer. Fractions containing the purified protein of interest, as determined by SDS-PAGE (12.5%) and Coomassie staining, were pooled and dialyzed against dialysis buffer (25 mM sodium phosphate, 25 mM sodium chloride) overnight at 4° C. The pH of all buffers was adjusted from 7.3 to 7.8 depending on the theoretical pI of each protein. Protein concentration was measured spectrophotometrically using A$_{280}$ 0.1% values (His$_6$PseA, 1.254; His$_6$LegA, 1.288; His$_6$LegM, 1.086; and those values described by Schoenhofen et al., 2006a; 2006b; 2009).

Example 2

Production of Precursor Compounds

The precursor compounds 1, 3, 5, 7, 9, and 11 were prepared. Compounds 1 (Example 4), 5 (Example 6), and 11 (Example 9) were enzymatically produced and purified according to previously published methods (Schoenhofen et al., 2006a; 2009; Karwaski et al., 2002). For example, compound 1 was prepared by the methods described by Schoenhofen et al (2006a). The CMP-pseudaminic acid enzymatic reaction was then passed through an Amicon Ultra-15 (10,000 MWCO) filter membrane before purification. The filtered CMP-pseudaminic acid sample was then lyophilized and desalted/purified using a Superdex Peptide 10/300 GL (GE Healthcare) column in 25 mM ammonium bicarbonate, pH 7.9. For further purity, elution fractions containing CMP-pseudaminic acid from above were subjected to anion-exchange chromatography (Mono Q 4.6/100 PE, GE Healthcare) using ammonium bicarbonate pH 7.9. Quantification of CMP-pseudaminic acid preparations was determined using the molar extinction coefficient of CMP ($\epsilon 260 = 7,400$). The pure fractions were diluted with water, and sodium hydroxide was added to give approximately 2 molar equivalents of NaOH for every mole of CMP-pseudaminic acid. After lyophilization, CMP-sugars remain in sodium form.

Compounds 3 (Example 5), 7 (Example 7), and 9 (Example 8) were produced as described below. Reaction mixtures for each of compounds 3, 7, and 9 were as follows:

a. His$_6$PseA reactions for the production of compound 3 (CMP-Pse5NHAc7NHAm) contained 0.8 mM compound 1 (CMP-Pse5NHAc7NHAc), 8 mM L-Gln or other amino acid, 2.4 mM ATP, 4 mM MgCl$_2$, and 1 mM DTT with 0.6 to 0.8 mg/ml His$_6$PseA (of Example 1) in dialysis buffer.

b. His$_6$LegA reactions for the production of compound 7 (CMP-Leg5NHAm7NHAc) contained 0.8 mM compound 5 (CMP-Leg5NHAc7NHAc), 8 mM L-Gln or other amino acid, 2.4 mM ATP, and 4 mM MgCl$_2$ with 0.6 to 0.8 mg/ml His$_6$LegA (of Example 1) in dialysis buffer.

c. His$_6$LegM reactions for the production of compound 9 (CMP-Leg5NHAmNMe7NHAc) contained 1 mM compound 7 (CMP-Leg5NHAm7NHAc) and 1.25 mM SAM, with 0.5 to 1 mg/ml His$_6$LegM (of Example 1) in dialysis buffer.

All chemicals used were purchased from Sigma.

Reactions mixtures for the production of compounds 3, 7, and 9 were incubated overnight at 37° C. Reaction mixtures were then passed through an Amicon Ultra-15 (10,000 molecular weight cut-off) or Ultra-4 (5,000 molecular weight cut-off) filter membrane before analysis. As required, CMP-nonulosonates were lyophilized and desalted/purified using a Superdex Peptide 10/300 GL (Amersham Biosciences) column in ammonium bicarbonate, pH 7.9. For further purity, the CMP-nonulosonate samples above were subjected to anion-exchange chromatography (Mono Q 4.6/100 PE, Amersham Biosciences) using ammonium bicarbonate pH 7.9.

Quantification of CMP-nonulosonate sugar preparations was determined using the molar extinction coefficient of CMP ($\epsilon_{260} = 7,400$). Two molar equivalents of either NaOH or NaCl were added to final CMP-nonulosonate preparations, which were then diluted 5× with water and lyophilized.

For structural characterization of compounds 3 and 7, purified material was dissolved in >99% D$_2$O, Structural analysis was performed using a Varian Inova 500 MHz ($^1$H) spectrometer with a Varian Z-gradient 3 mm probe, or a Varian 600 MHz ($^1$H) spectrometer with a Varian 5 mm Z-gradient probe. All spectra were referenced to an internal acetone standard ($\delta_H$ 2.225 ppm and $\delta_C$ 31.07 ppm). Results are shown in Tables 1-2.

TABLE 1

NMR chemical shifts δ (ppm) for CMP-5-acetamido-7-acetamidino-3,5,7,9-tetradeoxy-L-glycero-L-manno-nonulosonic acid (CMP-Pse5NHAc7NHAm, compound 3).

| H3ax | 1.66 | C2 | 101.0 |
| H3eq | 2.24 | C3 | 37.0 |
| H4 | 4.27 | C4 | 65.7 |
| H5 | 4.32 | C5 | 49.8 |
| H6 | 4.35 | C6 | 72.4 |
| H7 | 3.88 | C7 | 59.2 |
| H8 | 4.30 | C8 | 68.7 |
| H9 | 1.26 | C9 | 17.8 |

TABLE 2

NMR chemical shifts δ (ppm) for CMP-5-acetamidino-7-acetamido-3,5,7,9-tetradeoxy-D-glycero-D-galacto-nonulosonic acid (CMP-Leg5NHAm7NHAc, compound 7).

| H3ax | 1.68 | C2 | 100.9 |
| H3eq | 2.52 | C3 | 42.0 |
| H4 | 4.13 | C4 | 68.3 |
| H5 | 3.50 | C5 | 57.1 |
| H6 | 4.45 | C6 | 71.3 |
| H7 | 3.78 | C7 | 55.6 |
| H8 | 4.06 | C8 | 65.8 |
| H9 | 1.12 | C9 | 19.4 |

In the production of CMP-Pse5NHAc7NHAm (compound 3) and CMP-Leg5NHAm7NHAc (compound 7), the enzymes PseA and LegA, respectively, appeared to exhibit characteristics similar to glutamine-dependent amidotransferases (Gn-ATs). Gn-AT enzymes generate ammonia from the glutamine amide nitrogen and transfer it to an acceptor, producing glutamate and an aminated product (Massiere and Badet-Denisot, 1998). For some, Gn-AT enzymes, one molecule of ATP is required in the reaction to adenylate or phosphorylate the acceptor prior to product formation. Similar to Gn-AT enzymes, PseA and LegA catalyzed the production of compound 3 from 1 (CMP-Pse5NHAc7NHAc) and compound 7 from 5 (CMP-Leg5NHAc7NHAc), respectively, in the presence of L-Gln and ATP. ATP was absolutely required for the reaction to occur and could not be effectively replaced by other NTP donors. In the presence of ATP and substrate, with no nitrogen donor added, some product formation was observed, likely attributable to pre-activated or pre-charged enzyme from purification. This background activity was subtracted from all experimental results obtained prior to interpretation of data. Similar to many other Gn-AT enzymes, PseA and LegA could utilize exogenous ammonia as the nitrogen donor. Importantly, PseA and LegA differed greatly from Gn-AT enzymes in that several L-amino acids (Asp, Arg, Ser, Gly, Gln, Asn, Ile, His, Val, Met, Leu, Ala, Glu) could be utilized as a nitrogen donor, as opposed to Gn-AT enzymes which have only been reported to utilize Gln or Asn (Massiere and Badet-Denisot, 1998) as nitrogen donors. To our understanding, this is the first report of such an enzyme function and suggests a different catalytic mechanism to that proposed for the Gn-AT family of enzymes, especially since the α-carbon nitrogen of amino acids would be utilized by PseA and LegA as opposed to Gn-AT enzymes that utilize the amino acid side chain nitrogen. In general, PseA reactions resulted in approximately 30% product conversion, suggesting feedback inhibition, whereas LegA reactions resulted in nearly 100% product conversion.

The LegM enzyme catalyzed the formation of 9 (CMP-Leg5NHAmNMe7NHAc) from 7 in an S-adenosyl methionine (SAM)-dependent manner. Although most SAM-dependent methyltransferases are inhibited by the reaction byproduct S-adenosyl-L-homocysteine (SAH) (Aktas and Narberhaus, 2009), LegM did not appear to be inhibited by SAH as product conversion of approximately 80-90% could be attained. Interestingly, we tried similar reactions with Lpg0747 from *Legionella pneumophila* str. Philadelphia 1, but no detectable activity was observed, possibly due to SAH feedback inhibition. As mentioned in Example 1, the legM gene contained a poly-G tract in the middle, allowing regulation of protein expression by phase variation. The lpg0747 sequence does not contain a similar poly-G tract. This difference may explain the varied response of Lpg0747 and LegM to SAH, as Lpg0747 activity would rely on SAH feedback control, whereas LegM activity may be regulated at the transcriptional level by poly-G tract induced phase variation Example 3

Characterization of Precursor Compounds

Precursor compounds prepared in Example 2 were characterized using CE-MS analysis.

For CE-MS, mass spectra were acquired using an API3000 mass spectrometer (Applied Biosystems/Sciex, Concord, ON, Canada). CE was performed using a Prince CE system (Prince Technologies, Netherlands). CE separation was obtained on a 90 cm length of bare fused-silica capillary (365 um OD×50 um ID) with CE-MS coupling using a liquid sheath-flow interface and isopropanol:methanol (2:1) as the sheath liquid. An aqueous buffer comprising 30 mM morpholine (adjusted to pH9 with formic acid) was used for all experiments in the negative-ion mode. Results verifying the production of each CMP-nonulosonate precursor 1, 3, 5, 7, 9 and 11 are shown in Table 3, where observed m/z ions from CE-MS correspond accurately to the calculated masses.

TABLE 3

CE-MS data (negative ion mode) of CMP-nonulosonate sugars (precursor compounds) prepared. The m/z ions indicated here were not present in negative control samples (data not shown).

| Compound | | Observed m/z ion | Calculated mass | Formula (M) | Comments |
| --- | --- | --- | --- | --- | --- |
| 1 | CMP-Pse5NHAc7NHAc | 638.2 | 638.2 | C22 H34 O15 N5 P | M – H |
| 3 | CMP-Pse5NHAc7NHAm | 637.4 | 637.2 | C22 H35 O14 N6 P | M – H |
| 5 | CMP-Leg5NHAc7NHAc | 638.2 | 638.2 | C22 H34 O15 N5 P | M – H |
| 7 | CMP-Leg5NHAm7NHAc | 637.2 | 637.2 | C22 H35 O14 N6 P | M – H |
| 9 | CMP-Leg5NHAmNMe7NHAc | 651.4 | 651.2 | C23 H37 O14 N6 P | M – H |
| 11 | CMP-Neu5NHAc | 613.2 | 613.1 | C20 H31 O16 N4 P | M – H |

Figure 4:
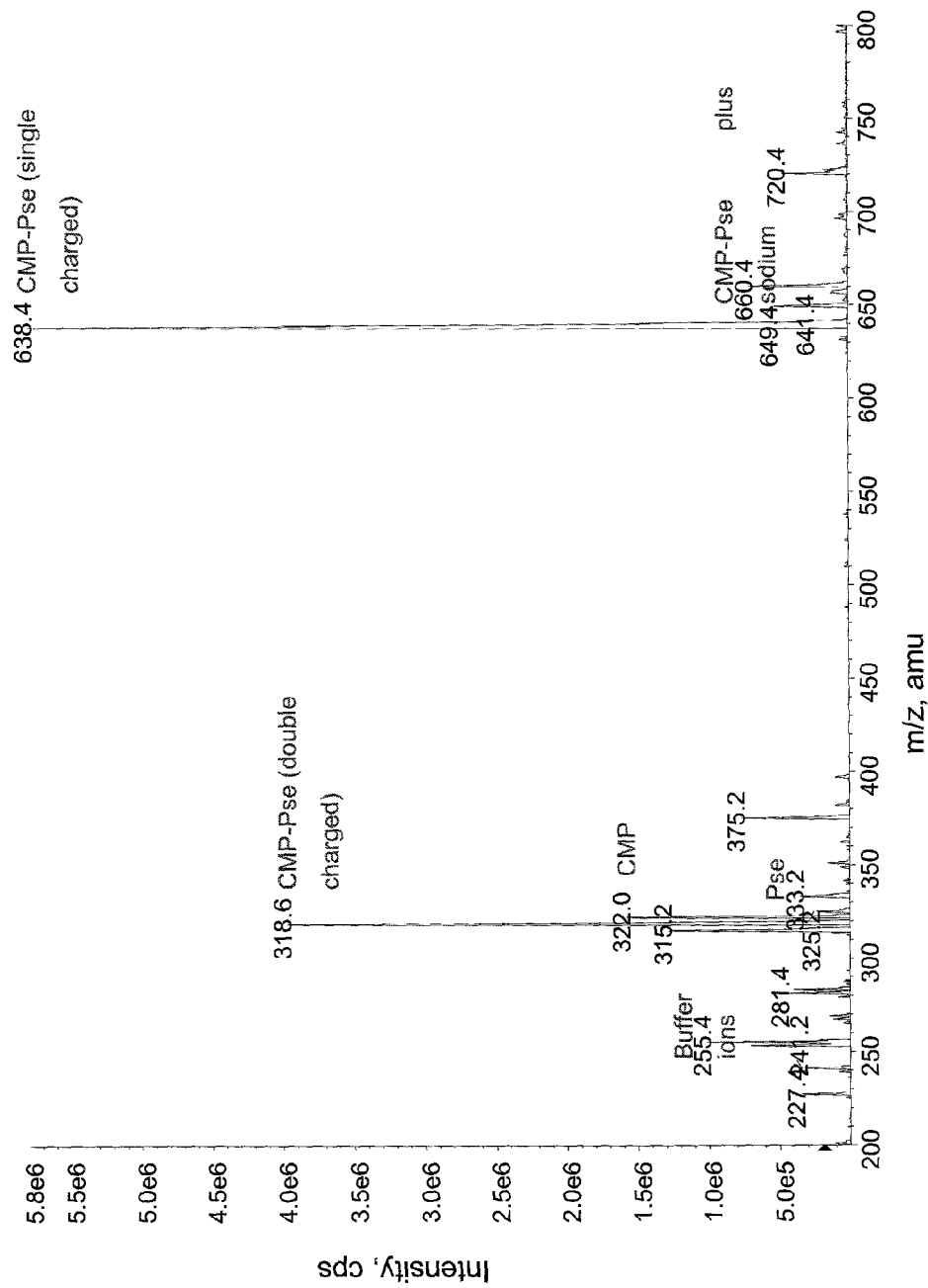
FIG. 4 shows a mass spectrometry (MS) spectrum of a precursor molecule, purified CMP-pseudaminic acid (CMP-Pse), after re-suspension in water; some dissociation of CMP and Pse are observed due to the instability of CMP-sugars in the absence of salt.

Additionally, FIG. 4 shows MS data of the purified CMP-pseudaminic acid in water, which indicates that the material is very clean. While some free CMP and pseudaminic acid can be observed in FIG. 4, this is due to the instability of CMP-sugars in the absence of salt; this dissociation is significantly reduced if resuspended in buffer containing sodium (data not shown). Similar results were obtained for other precursor compounds (data not shown).

Example 4

Production of Pse5NHAc7NHAc 2-ene

Compound 2 was produced in accordance with the following reaction scheme:

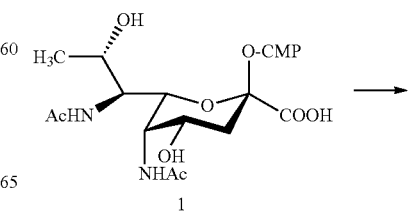

1

23

-continued

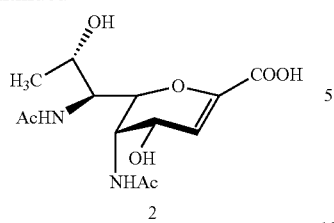

2

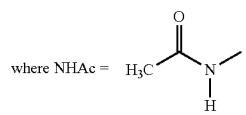

where NHAc =

Compound 1 was heated for 3 h at 105° C. in dry N,N'-dimethylformamide (DMF; 1 ml/mg). After cooling, the mixture was centrifuged at about 2000 rpm for 20 min and the supernatant was diluted 5× with water, then lyophilized. Further purification of compound 2 was performed by ion-exchange chromatography (MonoQ 4.6/100 PE, GE Healthcare) using ammonium bicarbonate buffer. Approximately two molar equivalents of NaOH was added to the purified compound, which was then diluted 5× with water and lyophilized.

Quantitation of compound 2 was performed using NMR by comparison to an internal standard; $^1$H NMR spectrum was acquired and the integrals calculated for the C-6 CH$_3$ proton region of rhamnose (internal standard) were compared to those calculated for the C-9 CH$_3$ proton region of 2.

For structural characterization of compound 2, purified material was dissolved in >99% D$_2$O, Structural analysis was performed using a Varian Inova 500 MHz ($^1$H) spectrometer with a Varian Z-gradient 3 mm probe, or a Varian 600 MHz ($^1$H) spectrometer with a Varian 5 mm gradient probe. All spectra were referenced to an internal acetone standard ($\delta_H$ 2.225 ppm and $\delta_C$ 31.07 ppm). Results are shown in Table 4.

TABLE 4

NMR chemical shifts δ (ppm) and coupling constants for the 5,7-diacetamido-3,5,7,9-tetradeoxy-L-glycero-L-manno-non-2-enonate (Pse5NHAcTNHAc 2-ene) compound.

| H3 | 5.59 ($J_{3,4}$ 1.8; $J_{3,5}$ 1.8) | C3 | 109.4 |
|----|---------------------------------------|-----|-------|
| H4 | 4.7 ($J_{4,5}$ 5.7) | C4 | 65.6 |
| H5 | 4.38 ($J_{5,6}$ 0) | C5 | 46.3 |
| H6 | 4.17 ($J_{6,7}$ 10) | C6 | 77 |
| H7 | 4.26 ($J_{7,8}$ ?) | C7 | 54.4 |
| H8 | 4.27 ($J_{8,9}$ 6.4) | C8 | 68 |
| H9 | 1.16 | C9 | 16.8 |

The $^1$H NMR spectra (data not shown) showed complete disappearance of the two H-3 resonances at δ 1.60 and 2.20 ppm and replacement by a new peak at δ 5.59 ppm, indicative of the formation of free CMP and 5,7-diacetamido-3,5,7,9-tetradeoxy-L-glycero-L-manno-non-2-enonate.

24

Example 5

Production of Pse5NHAc7NHAm 2-ene

Compound 4 was produced in accordance with the following reaction scheme:

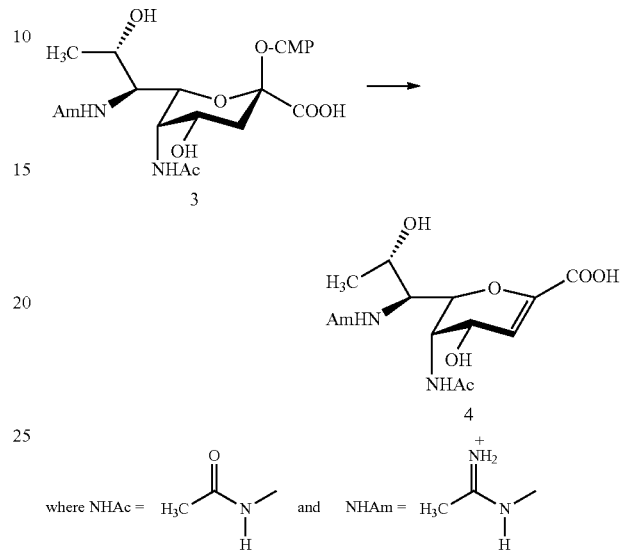

Compound 3 was heated for 3 at 105° C. in dry N,N-dimethylformamide (DMF; 1 ml/mg). After cooling, the mixture was centrifuged at about 2000 rpm for 20 min and the supernatant was diluted 5× with water, then lyophilized. Further purification of compound 4 was performed by ion-exchange chromatography (MonoQ 4.6/100 PE, GE Healthcare) using ammonium bicarbonate buffer. Approximately two molar equivalents of NaCl was added to the purified compound, which was then diluted 5× with water and lyophilized.

Example 6

Production of Leg5NHAc7NHAc 2-ene

Compound 6 was produced in accordance with the following reaction scheme:

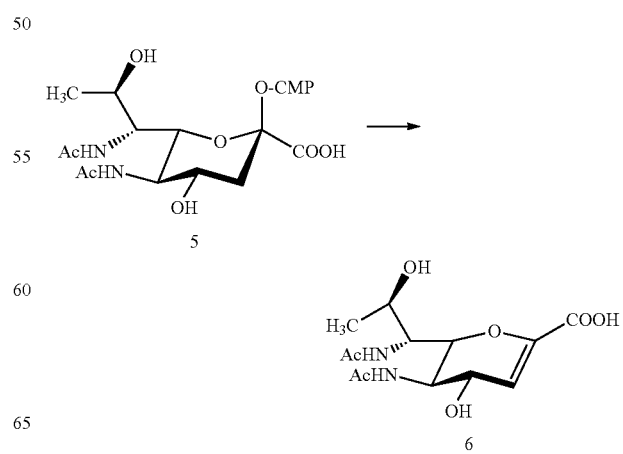

where NHAc = 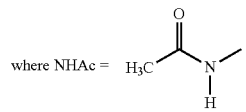

Compound 5 was heated for 3 h at 105° C. in dry N,N'-dimethylformamide (DMF; 1 ml/mg). After cooling, the mixture was centrifuged at about 2000 rpm for 20 min and the supernatant was diluted 5× with water, then lyophilized. Further purification of compound 6 was performed by ion-exchange chromatography (MonoQ 4.6/100 PE, GE Healthcare) using ammonium bicarbonate buffer. Approximately two molar equivalents of NaOH was added to the purified compound, which was then diluted 5× with water and lyophilized.

Quantitation of compound 6 was performed using NMR by comparison to an internal standard; $^1$H NMR spectrum was acquired and the integrals calculated for the C-6 CH$_3$ proton region of rhamnose (internal standard) were compared to those calculated for the C-9 CH$_3$ proton region of 6.

For structural characterization of compound 6, purified material was dissolved in >99% D$_2$O, Structural analysis was performed using a Varian Inova 500 MHz ($^1$H) spectrometer with a Varian Z-gradient 3 mm probe, or a Varian 600 MHz ($^1$H) spectrometer with a Varian 5 mm Z-gradient probe. All spectra were referenced to an internal acetone standard ($\delta_H$ 2.225 ppm and ($\delta_C$ 31.07 ppm). Results are shown in Table 5.

TABLE 5

NMR chemical shifts δ (ppm) and coupling constants for the 5,7-diacetamido-3,5,7,9-tetradeoxy-D-glycero-D-galacto-non-2-enonate (Leg5NHAc7NHAc 2-ene) compound.

| H3 | 5.68 | ($J_{3,4}$ 2.1) | C3 | 109.6 |
| H4 | 4.4 | ($J_{4,5}$ 10.3) | C4 | 69.7 |
| H5 | 3.89 | ($J_{5,6}$ 10) | C5 | 51.2 |
| H6 | 4.4 | ($J_{6,7}$ 0) | C6 | 76.2 |
| H7 | 3.92 | ($J_{7,8}$ 9.4) | C7 | 54.7 |
| H8 | 4.01 | ($J_{8,9}$ 6.3) | C8 | 67 |
| H9 | 1.19 | | C9 | 20.5 |

Example 7

Production of Leg5NHAm7NHAc 2-ene

Compound 8 was produced in accordance with the following reaction scheme:

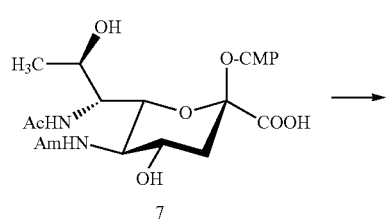

7

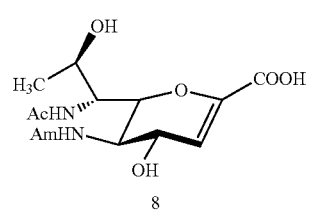

8 where NHAc = 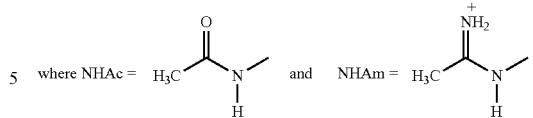

Compound 7 was heated for 3 h at 105° C. in dry N,N'-dimethylformamide (DMF; 1 ml/mg). After cooling, the mixture was centrifuged at about 2000 rpm for 20 min and the supernatant was diluted 5× with water, then lyophilized. Further purification of compound 8 was performed by ion-exchange chromatography (MonoQ 4.6/100 PE, GE Healthcare) using ammonium bicarbonate buffer. Approximately two molar equivalents of NaCl was added to the purified compound, which was then diluted 5× with water and lyophilized.

Quantitation of compound 8 was performed using NMR by comparison to an internal standard; $^1$H NMR spectrum was acquired and the integrals calculated for the C-6 CH$_3$ proton region of rhamnose (internal standard) were compared to those calculated for the C-9 CH$_3$ proton region of 8.

For structural characterization of compound 8, purified material was dissolved in >99% D$_2$O, Structural analysis was performed using a Varian Inova 500 MHz ($^1$H) spectrometer with a Varian Z-gradient 3 mm probe, or a Varian 600 MHz ($^1$H) spectrometer with a Varian 5 mm Z-gradient probe. All spectra were referenced to an internal acetone standard ($\delta_H$ 2.225 ppm and $\delta_C$ 31.07 ppm). Results are shown in Table 6.

TABLE 6

NMR chemical shifts δ (ppm) and coupling constants for the 5-acetamidino-7-acetamido-3,5,7,9-tetradeoxy-D-glycero-D-galacto-non-2-enonate (Leg5NHAm7NHAc 2-ene) compound.

| H3 | 5.71 | ($J_{3,4}$ 2.1) | C3 | 108.9 |
| H4 | 4.57 | ($J_{4,5}$ ~9) | C4 | 69.5 |
| H5 | 3.72 | ($J_{5,6}$ 10.4) | C5 | 54.8 |
| H6 | 4.54 | ($J_{6,7}$ 0) | C6 | 75.2 |
| H7 | 3.93 | ($J_{7,8}$ 9.4) | C7 | 54.8 |
| H8 | 4.05 | ($J_{8,9}$ 6.3) | C8 | 66.5 |
| H9 | 1.19 | | C9 | 20.4 |

Example 8

Production of Leg5NHAmNMe7NHAc 2-ene

Compound 10 was produced in accordance with the following reaction scheme:

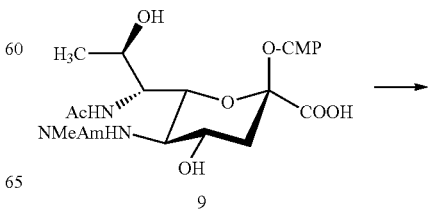

9

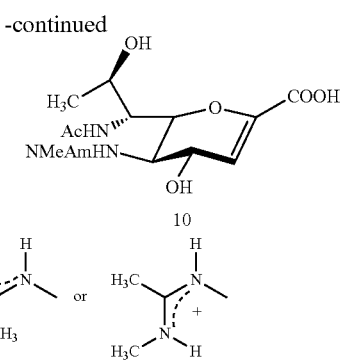

Compound 9 was heated for 2 h at 105° C. in dry N,N'-dimethylformamide (DMF; 1 ml/mg). After cooling, the mixture was centrifuged at about 2000 rpm for 20 min and the supernatant was diluted 5× with water, then lyophilized. Further purification of compound 10 was performed by ion-exchange chromatography (MonoQ 4.6/100 PE, GE Healthcare) using ammonium bicarbonate buffer. Approximately two molar equivalents of NaCl was added to the purified compound, which was then diluted 5× with water and lyophilized.

Example 9

Production of Neu5NHAc 2-ene

Compound 12 was produced in accordance with the following reaction scheme:

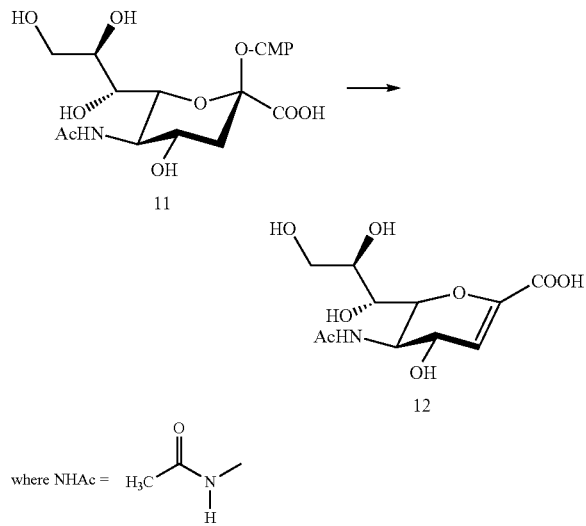

Compound 11 was heated for 6 h at 105° C. in dry N,N'-dimethylformamide (DMF; 1 ml/mg). After cooling, the mixture was centrifuged at about 2000 rpm for 20 min and the supernatant was diluted 5× with water, then lyophilized. Further purification of compound 12 was performed by ion-exchange chromatography (MonoQ 4.6/100 PE, GE Healthcare) using ammonium bicarbonate buffer. Approximately two molar equivalents of NaCl was added to the purified compound, which was then diluted 5× with water and lyophilized.

For structural characterization of compound 12, purified material was dissolved in >99% $D_2O$, Structural analysis was performed using a Varian Inova 500 MHz ($^1$H) spectrometer with a Varian Z-gradient 3 mm probe, or a Varian 600 MHz ($^1$H) spectrometer with a Varian 5 mm Z-gradient probe. All spectra were referenced to an internal acetone standard ($\delta_H$ 2.225 ppm and $\delta_C$ 31.07 ppm). Results are shown in Table 7.

TABLE 7

NMR chemical shifts δ (ppm) and coupling constants for the 5-acetamido-3,5-dideoxy-D-glycero-D-galacto-non-2-enonate (Neu5NHAc 2-ene) compound.

| | | | |
|---|---|---|---|
| H3 | 5.69 ($J_{3,4}$ 2.36) | C3 | 108.7 |
| H4 | 4.47 ($J_{4,5}$ 8.82) | C4 | 68.3 |
| H5 | 4.06 ($J_{5,6}$ 9.84) | C5 | 50.9 |
| H6 | 4.21 | C6 | 76.4 |
| H7 | 3.60 ($J_{7,8}$ 9.35) | C7 | |
| H8 | 3.94 ($J_{8,9}$ 2.8; $J_{8,9'}$ 6.3) | C8 | |
| H9 | 3.89 | | |
| H9' | 3.64 | | |

These values agree with previously published results (Beau et al., 1984).

Example 10

Characterization of non-2-enonate Compounds

Non-2-enonate compounds prepared in Examples 4-9 were characterized using exact mass analysis.

The exact mass analysis was performed on a Waters QTOF 2, using positive ions electrode spray. An internal mass standard was added to each sample and the samples were introduced to the MS via a flow injection method. The MS data was collected using Masslynx 4.1 and the molecular formula was deduced using the same software package. The error threshold arbitrary set at 30 ppm and no isotope fitting were used in the molecular formula determination. Results verifying the production of each non-2-enonate compound 2, 4, 6, 8, 10 and 12 are shown in Table 8, where observed m/z ions from exact mass analysis correspond accurately to their calculated mass.

TABLE 8

Exact mass analysis (positive ion mode) of certain non-2-enonate compounds prepared. The m/z ions indicated here were not present in negative control samples (data not shown).

| Sample | | Observed m/z ion | Calculated mass | Formula (M) | Comments |
|---|---|---|---|---|---|
| Pse5NHAc7NHAc 2-ene | 2 | 339.1127 | 339.1168 | C13 H20 O7 N2 | M + Na |
| Pse5NHAc7NHAm 2-ene | 4 | 338.1332 | 338.1328 | C13 H21 O6 N3 | M + Na |

TABLE 8-continued

Exact mass analysis (positive ion mode) of certain non-2-enonate compounds prepared. The m/z ions indicated here were not present in negative control samples (data not shown).

| Sample | | Observed m/z ion | Calculated mass | Formula (M) | Comments |
|---|---|---|---|---|---|
| Leg5NHAc7NHAc 2-ene | 6 | 339.1127 | 339.1168 | C13 H20 O7 N2 | M + Na |
| Leg5NHAm7NHAc 2-ene | 8 | 316.1471 | 316.1509 | C13 H21 O6 N3 | M + H |
| Leg5NHAmNMe7NHAc 2-ene | 10 | 330.1666 | 330.1665 | C14 H23 O6 N3 | M + H |
| Neu5NHAc 2-ene | 12 | 314.0905 | 314.0852 | C11 H17 O8 N1 | M + Na |

Example 11

Neuraminidase Inhibition Assays

The ability of compound 8 (from Example 7) to inhibit neuraminidase activity was evaluated.

The neuraminidase activity of influenza A neuraminidase samples (N1) was measured using a fluorescent neuraminidase assay as described by Potier et al (1979) and Buxton et al (2000) with slight modification (Hashem et al., 2009). In brief, equal amounts of neuraminidase samples (normalized by HA contents) containing various inhibitor concentrations (0.0005 µg/ml; 0.005 µg/ml; 0.05 µg/ml; 0.5 µg/ml; 5 µg/ml; 50 µg/ml; 200 µg/ml; 500 µg/ml) were incubated with MUNANA [2-(4-methylumbelliferyl)-α-D-N-acetyl-neuraminic acid] for 60 min at 37° C., followed by the addition of Stop Solution comprised of 0.14M NaOH in 83% Ethanol. Measurements of the fluorescent product were done using an excitation of 360 nm and emission of 448 nm.

Figure 5:
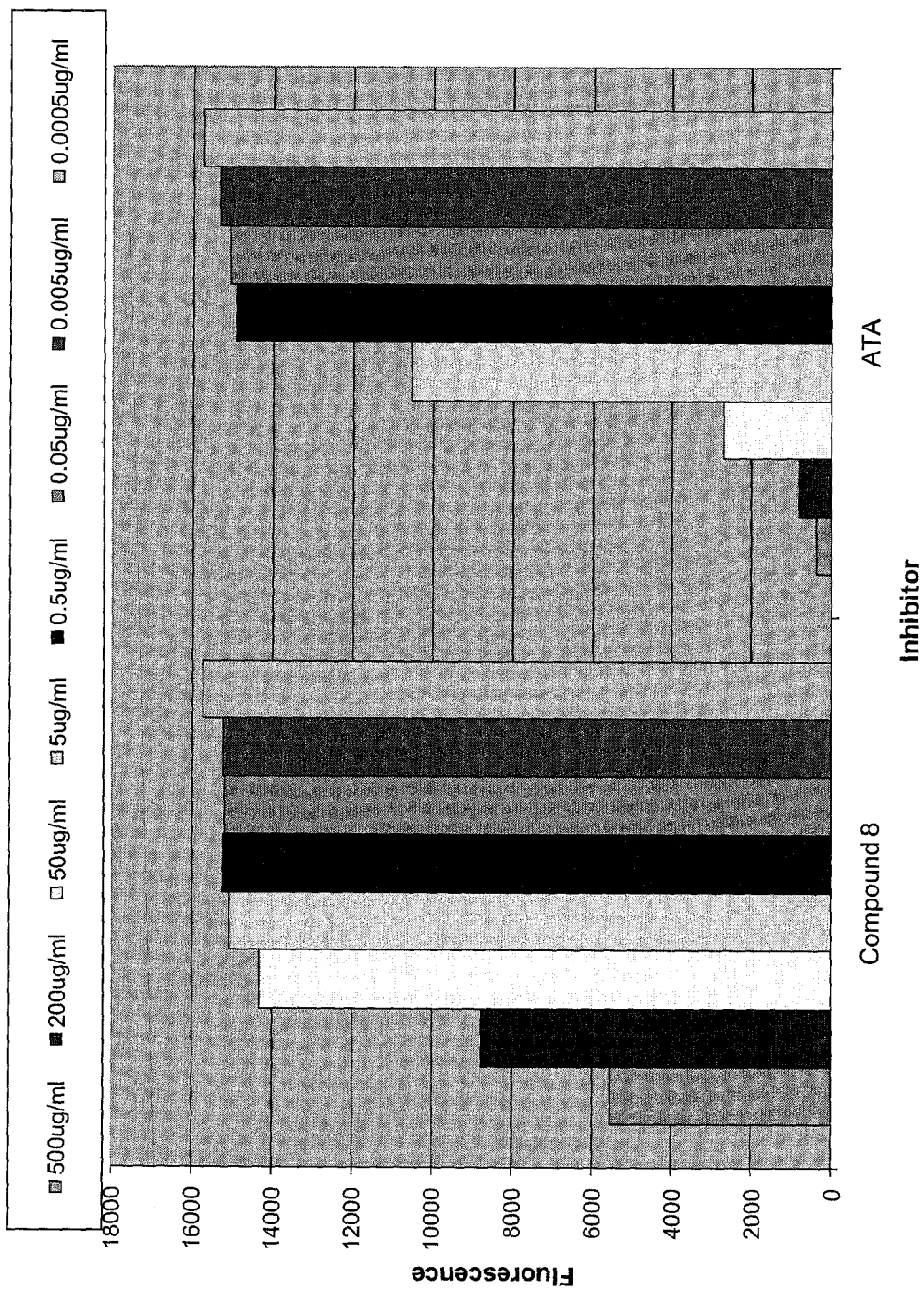
FIG. 5 is a bar graph comparing influenza A neuraminidase (N1) inhibition using various concentrations of compound 8 (Leg5NHAm7NHAc 2-ene) and ATA (Aurintricarboxylic acid; Hashem et al., 2009) in a MUNANA fluorescence based assay. ATA displays similar inhibition to compound 12 (Neu5NHAc 2-ene) or DANA.

Results are shown in FIG. 5 and Table 9. As seen in Table 9, inhibition of N1 enzyme could be achieved with compound 8 concentrations of 200 µg/ml, with little inhibition observed at 50 µg/ml. Even though compound 8 was not as potent an inhibitor as Aurintricarboxylic acid (ATA), a compound with a similar inhibitory profile to Neu5NHAc 2-ene (compound 12 or DANA; Hashem et al., 2009), this result demonstrates the ability of bacterial, sialic acid-like, non-2-enonate sugars to inhibit neuraminidase enzymes in vitro, with potential to be used as anti-viral therapeutics. Some neuraminidase inhibitors have been shown to exhibit selectivity in the type of neuraminidase they inhibit; for example, zanamivir is very selective for and is very potent against influenza neuraminidases, but much less potent against bacterial or mammalian neuraminidases (Colman, 1999). The present bacterial, sialic acid-like, non-2-enonate sugars may be more potent against bacterial or mammalian neuraminidases. To note, compound 12 appears to have modest potency against all 3 classes of neuraminidases (Colman, 1999).

TABLE 9

A comparison of influenza A neuraminidase (N1) inhibition using various concentrations of compound 8 (Leg5NHAm7NHAc 2-ene) and ATA (Aurintricarboxylic acid; Hashem et al., 2009) in a MUNANA fluorescence based assay.

| Inhibitor Concentration | Fluorescence Observed | |
|---|---|---|
| (µg/ml) | Compound 8 | ATA |
| 500 | 5554 | 378 |
| 200 | 8765 | 807 |
| 50 | 14315 | 2726 |
| 5 | 15074 | 10543 |
| 0.5 | 15242 | 14914 |
| 0.05 | 15212 | 15079 |
| 0.005 | 15222 | 15340 |
| 0.0005 | 15746 | 15741 |

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein, and throughout the application, are hereby incorporated by reference.

Aktas, M., and Narberhaus, F., *J. Bacteriol.*, 191, 2033 (2009).
Beau, J-M., et al., *Eur. J. Biochem.* 140, 203 (1984).
Beynon, L. M., et al., *Carbohydr. Res.* 256, 303 (1994).
Buxton, R. C., et al., *Anal. Biochem.* 280, 291 (2000)
Colman, P. M., *Protein Science* 3, 1687 (1994).
Colman, P. M., *J. Antimicrob. Chemother.* 44, 17 (1999).
Gubareva, L. V., et al, *Lancet* 355, 827 (2000).
Hashem, A. M., et al., *PLoS ONE* 4, e8350 (2009)
Hashii, N., et al., *Carbohydr. Res.* 338, 1055 (2003).
Hemeon, I., and Bennet, A. J., *Synthesis* 13, 1899 (2007)
Ishikawa, H., et al., *Agnew. Chem. Int. Ed.* 48, 1304 (2009).
Kajihara, Y., et al., *J. Org. Chem.* 60, 5732 (1995).
Karwaski, M-F., et al., *Protein Expr. Purif.* 25, 237 (2002).
Kazeera, T. N., and Shevelev, A. B., *Biochemistry (Mosc.)* 72, 485 (2007).
Knirel, Y. A., et al., *Adv. Carbohydr. Chem. Biochem.* 58, 371 (2003).
Kooistra, O., et al., *Eur. J. Biochem.* 269, 560 (2002).
Lagoja, I. M., and Clercq, E. D., *Med. Res. Reviews* 28, 1 (2008).
Lehmann, F., et al., *Cell. Mol. Life. Sci.* 63, 1331 (2006).
Li, X. et al., *Carbohydr. Res.* (2010), doi: 10.1016/j.carres.2010.04.008 (epub ahead of print)
Logan, S. M., et al., *Mot Microbiol.* 46, 587 (2002).
Logan, S. M., et al., *FEBS J.* 276, 1014 (2009).
Logan, S. M., *Microbiology* 152, 1249 (2006).
Massiere, F., and Badet-Denisot, M-A., *Cell. Mol. Life. Sci.* 54, 205 (1998).

Mazumder, K., et al., *Glycoconj. J.* 25, 345 (2008).
McNally, D. J., et al., *J. Biol. Chem.* 282, 14463 (2007).
Moscona, A., *N. Engl. J. Med.* 353, 1363 (2005).
Potier, M., et al., *Anal. Biochem.* 94, 287 (1979).
Schirm, M., et at., *Anal. Chem.* 77, 7774 (2005).
Schoenhofen, I. C., et al., *Glycobiology* 19, 715 (2009).
Schoenhofen, I. C., et al., *Glycobiology* 16, 8C (2006a).
Schoenhofen, I. C., et al., *J. Biol. Chem.* 281, 723 (2006b).
Shashkov, A. S., et al., *Carbohydr. Res.* 342, 653 (2007).
Soong, G., et al., *J. Clin. Invest* 116, 2297 (2006).
Thibault, P., et al., *J. Biol. Chem.* 276, 34862 (2001).
Twine, S. M., et al., *FEBS J.* 275, 4428 (2008).
Varki, A., et al, editors. Essentials of Glycobiology. 2nd edition, Cold Spring Harbor (NY): Cold Spring Harbor Laboratory Press; 2009. Chapter 14
Yamashita, M., et al., Antimicrobial Agents Chemotherapy 53, 186 (2009).
U.S. Provisional Patent Application 61/326,015
International Application No. PCT/CA2009/001800, filed Dec. 16, 2009.

The invention claimed is:

1. A compound of Formula 1

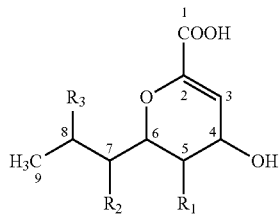

or a pharmaceutically acceptable salt or derivative thereof, wherein $R_1$ is NHAc,

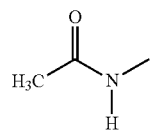 NHAm, 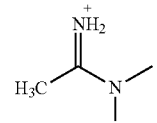 NHAmNMe(a),

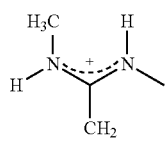 NHAmNMe(b), 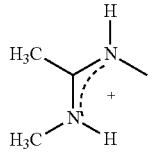,

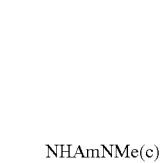 NHAmNMe(c), 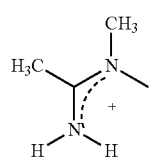 NHAmNMe(d),

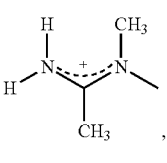 NHAmdiNMe(a), 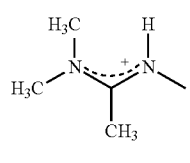,

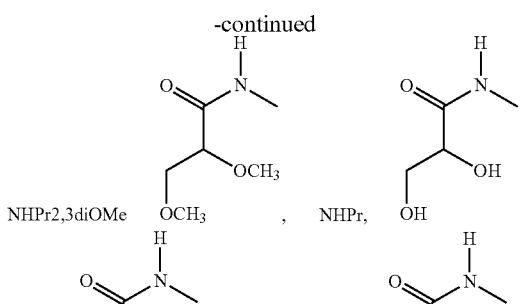 NHPr2,3diOMe, NHPr,

Glu, GluNMe, or

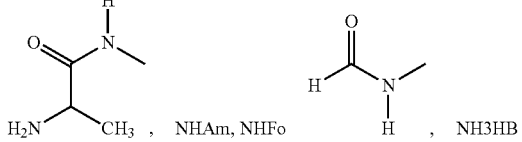 NH4HB; $R_2$ is NHAc, NHAla

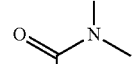 NHAm, NHFo 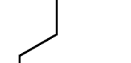, NH3HB

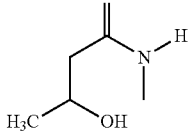, (N-acetyl-D-alanyl)amido

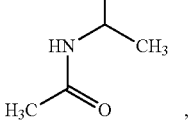, or NHPr; and $R_3$ is a hydroxyl or amino group.

2. The compound of claim 1, wherein the compound is

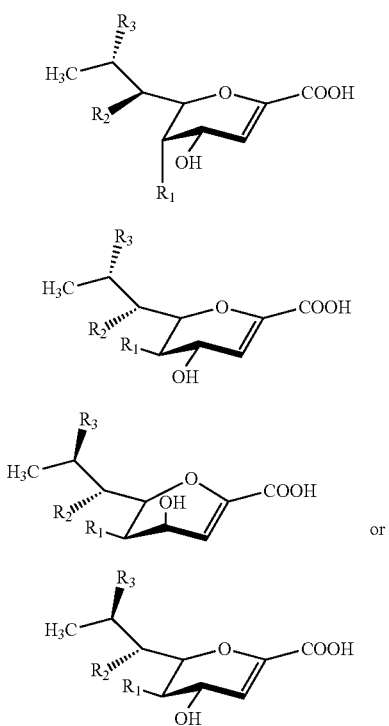

or a pharmaceutically acceptable salt or derivative thereof, wherein $R_1$, $R_2$ and $R_3$ are as defined in claim 1.

3. The compound of claim 1, wherein the compound is selected from the group consisting of:

5,7-diacetamido-3,5,7,9-tetradeoxy-L-glycero-L-manno-non-2-enonate (Pse5 NHAc7 NHAc 2-ene);

5-acetamido-7-acetamidino-3,5,7,9-tetradeoxy-L-glycero-L-manno-non-2-enonate (Pse5 NHAc7 NHAm 2-ene);

5-(2,3-di-O-methyl-propionyl)amino-7-acetamido-3,5,7,9-tetradeoxy-L-glycero-L-manno-non-2-enonate (Pse5 NHPr2,3 diOMe7 NHAc 2-ene);

5-(2,3-di-O-methyl-propionyl)amino-7-acetamidino-3,5,7,9-tetradeoxy-L-glycero-L-manno-non-2-enonate (Pse5 NHPr2,3 diOMe7 NHAm 2-ene);

5,7-diacetamido-3,5,7,9-tetradeoxy-L-glycero-D-galacto-non-2-enonate (8 eLeg5 NHAc7 NHAc 2-ene);

5-acetamido-7-N-(R)-3-hydroxybutanoyl-3,5,7,9-tetradeoxy-L-glycero-D-galacto-non-2-enonate (8 eLeg5 NHAc7 NH3HB 2-ene);

5-acetamido-7-N-formyl-3,5,7,9-tetradeoxy-L-glycero-D-galacto-non-2-enonate (8 eLeg5 NHAc7 NHFo 2-ene);

5,7-diacetamido-3,5,7,9-tetradeoxy-D-glycero-D-talo-non-2-enonate (4 eLeg5 NHAc7 NHAc 2-ene);

5-acetamidino-7-acetamido-3,5,7,9-tetradeoxy-D-glycero-D-talo-non-2-enonate (4 eLeg5 NHAm7 NHAc 2-ene);

5-di-N-methyl-acetamidino-7-acetamido-3,5,7,9-tetradeoxy-D-glycero-D-talo-non-2-enonate (4 eLeg5 NHAmdiNMe7 NHAc 2-ene);

5,7-diacetamido-8-amino-3,5,7,8,9-pentadeoxy-D-glycero-D-galacto-non-2-enonate (Leg5 NHAc7 NHAc8N 2-ene);

5,7-diacetamido-3,5,7,9-tetradeoxy-D-glycero-D-galacto-non-2-enonate (Leg5 NHAc7 NHAc 2-ene);

5-acetamido-7-N-(D-alanyl)-3,5,7,9-tetradeoxy-D-glycero-D-galacto-non-2-enonate (Leg5 NHAc7 NHAla 2-ene);

5-acetamidino-7-acetamido-3,5,7,9-tetradeoxy-D-glycero-D-galacto-non-2-enonate (Leg5 NHAm7 NHAc 2-ene);

5-N-methyl-acetamidino-7-acetamido-3,5,7,9-tetradeoxy-D-glycero-D-galacto-non-2-enonate (Leg5 NHAmNMe7 NHAc 2-ene);

5-di-N-methyl-acetamidino-7-acetamido-3,5,7,9-tetradeoxy-D-glycero-D-galacto-non-2-enonate (Leg5 NHAmdiNMe7 NHAc 2-ene);

5-(glutam-4-yl)amino-7-acetamido-3,5,7,9-tetradeoxy-D-glycero-D-galacto-non-2-enonate (Leg5 Glu7 NHAc 2-ene);

5-(N-methyl-glutam-4-yl)amino-7-acetamido-3,5,7,9-tetradeoxy-D-glycero-D-galacto-non-2-enonate (Leg5 GluNMe7 NHAc 2-ene); and pharmaceutically acceptable salts or derivatives thereof.

4. The compound of claim 1, wherein the compound is provided as a bioreversible derivative of the compound.

5. The compound of claim 4, wherein the bioreversible derivative is a C1-carboxylate ester of the compound.

6. A composition comprising one or more than one compound of claim 1 and a pharmaceutically acceptable carrier, diluent or excipient.

7. A method of producing non-2-enonate compounds or pharmaceutically acceptable salts or derivatives thereof, comprising: heating a CMP-nonulosonate compound, or a pharmaceutically acceptable salt or derivative thereof to a sufficient temperature and for a sufficient time so as to form the non-2-enonate compound.

8. The method of claim 7, wherein the method produces a compound of Formula I

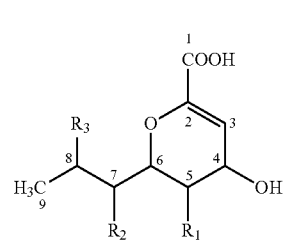

or a pharmaceutically acceptable salt or derivative thereof and wherein the method comprises the step of:
a) heating a compound of Formula VI

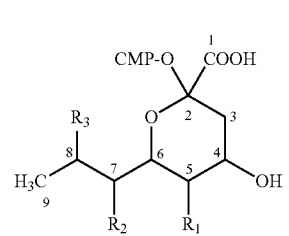

or a pharmaceutically acceptable salt or derivative thereof, to a sufficient temperature and for a sufficient time so as to form the compound of Formula I, wherein $R_1$ is NHAc, NHAm, NHAmNMe(a), NHAmNMe(b), NHAmNMe(c), NHAmNMe(d), NHAmdiNMe(a), NHPr2,3 diOMe, NHPr, Glu, GluNMe, or NH4HB; $R_2$ is NHAc, NHAla, NHAm, NHFo, NH3HB, (N-acetyl-D-alanyl)amido, or NHPr; and R3 is a hydroxyl or amino group.

9. The method of claim 7, wherein the method produces a compound of Formula VIII

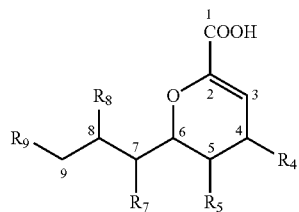

or a pharmaceutically acceptable salt or derivative thereof and wherein the method comprises the step of:

a) heating a compound of Formula VII

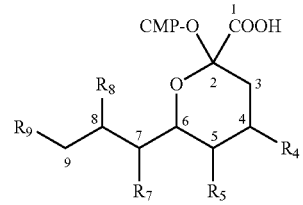

or a pharmaceutically acceptable salt or derivative thereof, to a sufficient temperature and for a sufficient time so as to form the sialic acid non-2-enonate derivative of formula VIII, wherein $R_4$ is selected from OH, O-acetyl, O-Fuc, O-Gal, or guanidino;

$R_5$ is selected from amino, N-acetyl, N-glycolyl, hydroxyl, N-acetimidoyl (acetamidino), N-glycolyl-0-acetyl, N-glycolyl-O-methyl, N-glycolyl-O-2-Neu5Gc, or N-azido-acetyl;

$R_7$ is selected from OH or O-acetyl;

$R_8$ is selected from OH, O-acetyl, O-methyl, O-sulfate, O-Sia, O-Glc, amino or azido; and $R_9$ is selected from OH, O-acetyl, O-lactyl, O-phosphate, O-sulfate, O-Sia, amino or azido.

10. The method of claim 7, further comprising a step of purifying the compounds.

11. A method of producing compound 3

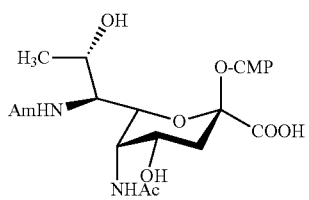

comprising contacting an enzyme of SEQ ID NO:1 with compound CMP-Pse5NHAc7NHAc in the presence of L-Gln or ammonia and ATP under suitable conditions for the production of compound 3.

12. A method of producing compound 7

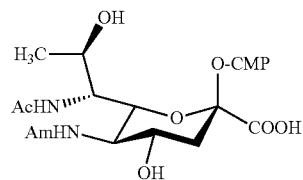

comprising contacting an enzyme of SEQ ID NO:4 with compound CMP-Leg5 NHAc7 NHAc in the presence of L-Gln or ammonia and ATP under suitable conditions for the production of compound 7.

13. A method of producing compound 9

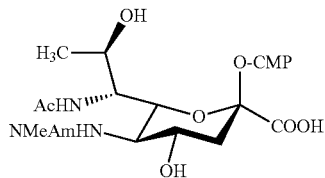

comprising contacting an enzyme of SEQ ID NO:7 with compound CMP-Leg5 NHAm7 NHAc in the presence of S-adenosylmethionine under suitable conditions for the production of compound 9.

14. A method of inhibiting sialidase or sialidase-like enzymes, comprising contacting the sialidase or sialidase-like enzyme with a compound of claim 1 or a composition of claim 6.

15. The method of claim 14, wherein the sialidase or sialidase-like enzymes is of viral, bacterial, or human origin.

16. The method of claim 14, wherein the compound is Leg5 NHAc7 NHAc 2-ene, Pse5 NHAc7 NHAc 2-ene, Leg5 NHAm7 NHAc 2-ene, or a combination thereof.

17. A method of treating bacterial or viral infections, comprising administering of claim 1 or a composition of claim 6 to a subject in need thereof.

* * * * *

SEQUENCE LISTING

```
<160> NUMBER OF SEQ ID NOS: 11

<210> SEQ ID NO 1
<211> LENGTH: 390
<212> TYPE: PRT
<213> ORGANISM: Artificial Sequence
<220> FEATURE:
<223> OTHER INFORMATION: PseA enzyme

<400> SEQUENCE: 1

Met Gly Ser Ser His His His His His His Gly Ser Met Lys Phe Cys
1               5                   10                  15

Lys Lys Cys Val Met Pro Asp Thr Lys Pro Asp Leu His Phe Asp Glu
            20                  25                  30

Glu Gly Val Cys Asp Ala Cys Arg Ser Gln Glu Ala Lys Asn Gln Asn
        35                  40                  45

Ile Asn Trp Gln Glu Arg Glu Lys Glu Phe Phe Glu Leu Ile Lys Lys
    50                  55                  60

Tyr Lys Lys His Pro Val Tyr Asp Cys Val Ile Gly Val Ser Gly Gly
65                  70                  75                  80

Lys Asp Ser Thr Phe Gln Val Val Lys Met Leu Glu Leu Gly Leu Asn
                85                  90                  95

Pro Leu Cys Val Cys Phe Glu Pro Ser Val Pro Thr Lys Ile Gly Arg
            100                 105                 110

Lys Asn Leu Asp Asn Leu Asn His Leu Gly Val Asp Leu Ile His Ile
        115                 120                 125

Lys Arg Asp Pro Lys Val Tyr Gln Lys Leu Ala Arg Glu Ala Phe Ile
    130                 135                 140

Arg Thr Gly Asp Asn Glu Trp Gln Asn His Leu Gly Ile Phe Thr Ser
145                 150                 155                 160

Val Pro Arg Ile Ala Val Asn Phe Gly Val Pro Leu Ile Ile Trp Gly
                165                 170                 175

Glu Ser Pro Gln Ile Glu Tyr Gly Gly Pro Ala Ser Ser Lys Asn Lys
            180                 185                 190

Asn Ile Leu Gly Arg Glu Trp Leu Glu Glu Phe Gly Gly Leu Leu Gly
        195                 200                 205

Asn Arg Ala Ser Asp Met Leu Gly Val Asn Gly Ile Thr Glu Lys Asp
    210                 215                 220

Leu Phe Leu Tyr Thr Tyr Pro Ser Asp Glu Glu Leu Gln Arg Val Gly
225                 230                 235                 240

Val Thr Gly Leu Phe Leu Gly Tyr Tyr Phe Lys Trp Asp Tyr Lys Lys
                245                 250                 255

Ile Leu Glu Ile Ser Lys Lys Tyr Gly Phe Leu Thr Leu Asp His Pro
            260                 265                 270

Val Glu Thr Thr Tyr Glu Asn Phe Glu Asn Leu Asp Cys Tyr Ser Asn
        275                 280                 285
```

```
His Val His Asp Tyr Leu Lys Tyr Cys Lys Tyr Gly Phe Gly Arg Ala
    290                 295                 300

Thr Asp Asn Ala Cys Leu Asp Ile Arg Leu Gly Tyr Ile Ser Arg Glu
305                 310                 315                 320

Glu Gly Val Arg Leu Ala Gln Lys Tyr Asp Gly Lys Pro Pro Lys Lys
                325                 330                 335

Ala Ile Lys Lys Tyr Leu Glu Phe Ser Gly Phe Ser Glu Glu Glu Phe
                340                 345                 350

Gln Lys Ile Val Asp Ser Phe Thr Asn Lys Lys Ile Phe Lys Arg Asp
            355                 360                 365

Glu Asn Gly Lys Phe Ile Arg Asp Tyr Asp Gly Ser Leu Val Arg Lys
    370                 375                 380

Asp Glu Cys Val Leu Lys
385             390

<210> SEQ ID NO 2
<211> LENGTH: 37
<212> TYPE: DNA
<213> ORGANISM: Artificial Sequence
<220> FEATURE:
<223> OTHER INFORMATION: NRC64

<400> SEQUENCE: 2
ggatccatga aattttgtaa aaaatgtgtg atgccag                              37

<210> SEQ ID NO 3
<211> LENGTH: 37
<212> TYPE: DNA
<213> ORGANISM: Artificial Sequence
<220> FEATURE:
<223> OTHER INFORMATION: NRC65

<400> SEQUENCE: 3
ctcgagtcat tttaaaacac actcgtcttt tcttacc                              37

<210> SEQ ID NO 4
<211> LENGTH: 385
<212> TYPE: PRT
<213> ORGANISM: Artificial Sequence
<220> FEATURE:
<223> OTHER INFORMATION: LegA enzyme

<400> SEQUENCE: 4

Met Gly Ser Ser His His His His His His Gly Ser Met Ile Tyr Cys
1               5                   10                  15

Asp His Cys Val Met Pro Asn Thr Arg Pro Gly Ile Asn Phe Thr Lys
                20                  25                  30

Asp Lys Glu Gly Lys Asn Ile Cys Ser Ala Cys Ile Asn His Lys Asn
            35                  40                  45

Lys Glu Asn Ile Asp Tyr Lys Ala Arg Phe Lys Glu Leu Glu Val Leu
    50                  55                  60

Cys Asp Lys Tyr Arg Arg Met Asn Gly Lys Phe Glu Tyr Asp Cys Ala
65                  70                  75                  80

Ile Ala Val Ser Gly Gly Lys Asp Ser His Phe Gln Val His Ile Met
                85                  90                  95

Lys Glu Lys Leu Gly Met Asn Pro Ile Leu Phe Ser Val Glu Asp Asn
            100                 105                 110

Phe Thr Met Thr Glu Ala Gly Lys Lys Asn Leu Lys Asn Leu Ser Glu
        115                 120                 125
```

```
Thr Phe Gly Cys His Ile Ile Ser Leu Lys Pro Asp Ile Lys Thr Gln
        130                 135                 140

Lys Lys Val Met Leu Lys Thr Phe Glu Lys Tyr Gly Lys Pro Thr Trp
145                 150                 155                 160

Phe Ile Asp Arg Leu Ile Tyr Ser Tyr Pro Phe Ala Met Ala Leu Lys
                165                 170                 175

Phe Asn Thr Pro Leu Leu Val Tyr Gly Glu Asn Val Ser Tyr Glu Tyr
                180                 185                 190

Gly Gly Ser Asp Thr Glu Glu Thr Pro Ser Ala Lys Glu Ile Phe Leu
            195                 200                 205

Asn Gly Val Ala Ser Asp Leu Asn Ile Asn Glu Phe Ile Asp Asp Glu
210                 215                 220

Ile Lys Glu Glu Asn Leu Gln Leu Phe Phe Asn Pro Asn Lys Asp Lys
225                 230                 235                 240

Leu Asp Lys Leu Asn Pro Ile Tyr Leu Ser Tyr Phe Val Lys Trp Asn
                245                 250                 255

Ser Tyr Ser Asn Tyr Ile Phe Ala Lys Ser Arg Gly Phe Thr Asp Leu
            260                 265                 270

Glu Gly Glu Trp Asp Arg Thr Met Cys Ala Glu Asn Phe Asp Gln Val
        275                 280                 285

Asp Ser Ile Gly Tyr Ile Leu His Ala Trp Met Lys Tyr Pro Lys Phe
290                 295                 300

Gly His Ala Cys Ala Ser Asp Tyr Ala Ala Arg Phe Val Arg Tyr Gly
305                 310                 315                 320

Leu Leu Ser Arg Lys Glu Ala Ile Glu Leu Val Gln Lys Arg Asp His
                325                 330                 335

Lys Leu Asp Asn Lys Cys Val Glu Asp Phe Cys Asn Phe Ile Gly Ile
            340                 345                 350

Ser Lys Thr Thr Phe Trp Lys Ile Val Glu Lys His Tyr Asn Met Asp
        355                 360                 365

Leu Phe Tyr Lys Asn Asp Phe Gly Glu Phe Lys Leu Lys Asn Lys Leu
    370                 375                 380

Gln
385

<210> SEQ ID NO 5
<211> LENGTH: 30
<212> TYPE: DNA
<213> ORGANISM: Artificial Sequence
<220> FEATURE:
<223> OTHER INFORMATION: NRC-97

<400> SEQUENCE: 5
ggatccatga tttattgtga tcactgcgtg                                  30

<210> SEQ ID NO 6
<211> LENGTH: 39
<212> TYPE: DNA
<213> ORGANISM: Artificial Sequence
<220> FEATURE:
<223> OTHER INFORMATION: NRC309

<400> SEQUENCE: 6
ctcgagttat tgtaatttgt tttttaattt aaattctcc                        39

<210> SEQ ID NO 7
<211> LENGTH: 235
<212> TYPE: PRT
```

<213> ORGANISM: Artificial Sequence
<220> FEATURE:
<223> OTHER INFORMATION: LegM enzyme

<400> SEQUENCE: 7

```
Met Gly Ser Ser His His His His His His Gly Ser Gln Asn Ser Leu
1               5                   10                  15

Glu Ala Tyr Thr Met Lys Tyr Asn Glu Asn Gly Tyr Gly Leu Leu Phe
            20                  25                  30

Pro Asp Gly His Val Val Arg Phe Tyr Glu Arg Ile Leu Lys Tyr Lys
        35                  40                  45

Leu Asn Lys Ile Asn Gly Asn Leu Leu Asp Phe Gly Cys Gly Asn Gly
50                  55                  60

Val His Ser Ala Tyr Phe Gln Ser Lys Gly Phe Lys Thr Phe Gly Ile
65                  70                  75                  80

Asp Ile Val Pro Ser Leu Lys Glu Ile Trp Glu Gln Asn Ile Ser Gly
                85                  90                  95

Gly Gly Tyr Cys Lys Ile Ile Glu Pro Asn Ser Ser Ile Lys Gly Leu
            100                 105                 110

Phe Asp Glu Asn Met Asp Ile Ile Phe Ala Asn Gln Ser Leu Tyr Tyr
        115                 120                 125

Ile Pro Leu Lys Glu Leu Lys Gln Asn Ile Leu Glu Phe Tyr Glu Leu
130                 135                 140

Leu Asn Thr Gly Gly Ile Leu Phe Ala Thr Met Met Ser Lys Lys Asn
145                 150                 155                 160

Tyr Tyr Phe Ser His Ser Gln Lys Glu Glu Lys Asn Gly Leu Ser Lys
                165                 170                 175

Val Glu Ile Asn Gly Arg Leu Asn Glu Thr Ser Phe Ile His Phe Ile
            180                 185                 190

Asp Lys Ala Glu Asp Leu Glu Asn Leu Phe Gln Pro Phe Glu Thr Leu
        195                 200                 205

Phe Leu Gly Asp Tyr Asp Pro Ile Asn Phe Tyr Asn Phe Glu Gly Ser
    210                 215                 220

Ala His His Tyr Ile Tyr Ile Gly Ile Lys Lys
225                 230                 235
```

<210> SEQ ID NO 8
<211> LENGTH: 43
<212> TYPE: DNA
<213> ORGANISM: Artificial Sequence
<220> FEATURE:
<223> OTHER INFORMATION: NRC308

<400> SEQUENCE: 8
ggatcccaaa actcattaga agcttataca atgaaatata atg          43

<210> SEQ ID NO 9
<211> LENGTH: 44
<212> TYPE: DNA
<213> ORGANISM: Artificial Sequence
<220> FEATURE:
<223> OTHER INFORMATION: NRC309

<400> SEQUENCE: 9
gaattcttat tttttaatac ctatataaat ataatggtgt gccg          44

<210> SEQ ID NO 10
<211> LENGTH: 59
<212> TYPE: DNA

```
<213> ORGANISM: Artificial Sequence
<220> FEATURE:
<223> OTHER INFORMATION: 1325/26-F

<400> SEQUENCE: 10 gaatttggg agcaaaatat tagcggagga ggatattgta aaattataga accaaattc      59

<210> SEQ ID NO 11
<211> LENGTH: 59
<212> TYPE: DNA
<213> ORGANISM: Artificial Sequence
<220> FEATURE:
<223> OTHER INFORMATION: 1325/26-R

<400> SEQUENCE: 11
gaatttggtt ctataatttt acaatatcct cctccgctaa tatttttgctc ccaaattc      59
```